US012712080B2

(12) United States Patent
Fallman et al.

(10) Patent No.: US 12,712,080 B2
(45) Date of Patent: Aug. 18, 2026

(54) DIALYSIS SYSTEM HAVING REDUCED VALVE NOISE

(71) Applicants: Vantive US Healthcare LLC, Deerfield, IL (US); Vantive Health GMBH, Glattpark (CH)

(72) Inventors: Oskar Erik Frode Styrbjörn Fallman, Lund (SE); Michael Pettersson, Malmö (SE); Jimmie Marcus Axel Hansson, Limhamn (SE); Per-Olof Borgqvist, Lund (SE)

(73) Assignees: Vantive US Healthcare LLC, Deerfield, IL (US); Vantive Health GMBH, Glattpark (CH)

( * ) Notice: Subject to any disclaimer, the term of this patent is extended or adjusted under 35 U.S.C. 154(b) by 197 days.

(21) Appl. No.: 18/528,418

(22) Filed: Dec. 4, 2023

(65) Prior Publication Data

US 2024/0181141 A1 Jun. 6, 2024

Related U.S. Application Data

(60) Provisional application No. 63/429,845, filed on Dec. 2, 2022.

(51) Int. Cl.
*G16H 50/20* (2018.01)
*A61M 1/14* (2006.01)
(Continued)

(52) U.S. Cl.
CPC .............. *G16H 50/20* (2018.01); *A61M 1/14* (2013.01); *A61M 1/1561* (2022.05); *A61M 1/1565* (2022.05); *A61M 1/159* (2022.05); *A61M 1/1601* (2014.02); *A61M 1/28* (2013.01); *A61M 1/282* (2014.02); *A61M 1/362265* (2022.05);
(Continued)

(58) Field of Classification Search
CPC ..... G16H 50/20; G16H 40/60; A61M 1/1565; A61M 1/1601; A61M 1/282; A61M 1/362265; A61M 1/1561; A61M 2205/18; A61M 1/14; A61M 2205/42; A61M 2205/50; A61M 2205/52; A61M 1/28; A61M 1/159; G06T 7/251;
(Continued)

(56) References Cited

U.S. PATENT DOCUMENTS 3,654,486 A * 4/1972 Cubert ................ H03K 3/2893 326/130
5,775,276 A * 7/1998 Yanai ....................... F01L 9/20 123/90.11

(Continued)

*Primary Examiner* — Thienvu V Tran
*Assistant Examiner* — Muaamar Qahtan Al-Taweel
(74) *Attorney, Agent, or Firm* — K&L Gates LLP

(57) ABSTRACT

Systems and methods are disclosed for reducing noise in solenoid valve activation and deactivation in peritoneal dialysis ("PD") systems. In at least one embodiment, the PD system operates with solenoid valves under the control of a control unit. The control unit takes measures to control the movement of the solenoid valve to minimize the amount of sound that occurs at impact during activation and deactivation of the valve. The measures include the slowing of the movement of the valve plunger within the valve coil. In one aspect, the valve plunger may be slowed down by applying voltage to the valve coil through pulse width modulation ("PWM").

16 Claims, 17 Drawing Sheets

(51) Int. Cl.

| | |
|---|---|
| ***A61M 1/16*** | (2006.01) |
| ***A61M 1/28*** | (2006.01) |
| ***A61M 1/36*** | (2006.01) |
| ***F16K 11/044*** | (2006.01) |
| ***F16K 31/06*** | (2006.01) |
| ***F16K 31/10*** | (2006.01) |
| ***F16K 31/52*** | (2006.01) |
| ***G06T 7/246*** | (2017.01) |
| ***G16H 40/60*** | (2018.01) |
| ***H01F 7/18*** | (2006.01) |

(52) U.S. Cl.

CPC ........ *F16K 11/044* (2013.01); *F16K 31/0627* (2013.01); *F16K 31/10* (2013.01); *F16K 31/52* (2013.01); *G06T 7/251* (2017.01); *G16H 40/60* (2018.01); *H01F 7/1844* (2013.01); *A61M 2205/18* (2013.01); *A61M 2205/42* (2013.01); *A61M 2205/50* (2013.01); *A61M 2205/52* (2013.01); *G06T 2207/20081* (2013.01)

(58) Field of Classification Search

CPC ......... G06T 2207/20081; F16K 11/044; F16K 31/0627; F16K 31/10; F16K 31/52; H01F 7/1844

See application file for complete search history.

(56) References Cited

U.S. PATENT DOCUMENTS

2002/0144683 A1* 10/2002 Gurnee ................ A61G 10/026 128/205.24
2002/0177237 A1* 11/2002 Shvets ................ F16K 37/0041 436/180
2004/0082908 A1* 4/2004 Whitehurst ........ A61N 1/36071 604/20
2005/0209563 A1* 9/2005 Hopping ............. A61M 1/1607 604/151
2009/0173682 A1* 7/2009 Robinson ........ A61M 1/362265 210/240
2018/0310391 A1* 10/2018 Hobro ..................... A61M 1/34

* cited by examiner 224
220
230
228
228p
222
226p
210
206l
226
206
204
194
202
208
204
206e
202s
200
202c

DIALYSIS SYSTEM HAVING REDUCED VALVE NOISE

PRIORITY CLAIM

This application claims priority to and the benefit as a non-provisional application of U.S. Provisional Patent Application No. 63/429,845, filed Dec. 2, 2022, the entire contents of which are hereby incorporated by reference and relied upon.

TECHNICAL FIELD

The present disclosure relates generally to medical fluid treatments, and in particular to dialysis fluid treatments that use valves for medical fluid control.

BACKGROUND

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal chamber. APD machines also allow for the dialysis fluid to dwell within the chamber and for the transfer of waste, toxins and excess water to take place. The source may include multiple liters of dialysis fluid including several solution bags.

APD machines pump used or spent dialysate from the patient's peritoneal cavity, though the catheter, to drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

Each of the above-identified dialysis modalities, except for CAPD (which typically does not involve machinery), uses automated valves to control whether dialysis fluid, blood or other fluid is able to flow or not flow. The valves also control the direction of fluid flow; such as where the fluid comes from or the destination to which the fluid flows. Different types of valves are used in dialysis system. One type of valve is used typically with a disposable cassette having a hard plastic part defining fluid flow paths and valve seats and one or more flexible membrane covering one or more side of the hard plastic part. The disposable cassette is typically loaded into a dialysis machine or cycler, which is able to close designated parts of the one or more plastic sheet against the valve seats to block fluid flow and to force or allow the plastic to move away from the valve seats to allow fluid flow.

Another type of automated valve is a pinch valve that instead pinches closed a tube carrying the dialysis fluid, blood or other fluid to block fluid flow. Here, a hard plastic disposable cassette is not needed, saving cost. There are generally two types of pinch valves, solenoid pinch valves and motorized pinch valves. Another type of automated valve is solenoid plunger valve. The solenoid plunger valve uses a plunger to move a lever that is pressed against a seat to stop the flow (or move the lever to press the seat cause the flow). One problem with solenoid pinch valves and solenoid plunger valves (collectively referred to herein as "solenoid valves") is noise. For example, solenoid plunger valves generally involve the energizing of a coil that moves a plunger within a housing. The plunger may be moved while the coil is energized to allow the tube to open for fluid flow. When energy is removed from the coil, a compressed spring is allowed to push the plunger in the opposite direction to occlude the tube against a stop or wall located on the opposing end of the tube. The plunger moving in either direction encounters an end-of-travel that involves the plunger contacting a fixed surface either directly or with the tube in between. The end-of-travel contacting creates noise. Especially for an APD treatment, which typically occurs at night while the patient sleeps, noise from solenoid valves may disturb the patient and be problematic.

Another issue with solenoid valves is knowing that the valve has opened when energized. That is, knowing that the energizing of the coil has actually moved the plunger (e.g., in a solenoid plunger valve) or actually removes the pinching of a tube (e.g., in a solenoid pinch valve) so that it no longer occludes a tube or fluid flow. Assuming that a valve is open when it is not is likely to create an undesirable situation.

For each of the above issues, an improved way to operate solenoid valves is needed.

SUMMARY

The present disclosure sets forth methodologies for operating solenoid valves for use in medical fluid systems, such as an automated peritoneal dialysis ("PD") system, which improves the usability of the valve. While the present system is described primarily in connection with PD, the improved solenoid valve operation of the present disclosure applies to machines used for any dialysis modality described herein, such as online HD, HF, HDF, and acute HD, HF, HDF. The improved solenoid valve operation of the present disclosure also applies to any medical fluid system in which a treatment fluid flow, or a patient fluid flow, is controlled via one or more valve.

In a PD example, the system includes a PD machine or cycler. The PD machine is described herein primarily as a durable system that attempts to limit disposable waster as much as possible, e.g., via the use of electromechanical piston pumps that pump medical or PD fluid through the body of the pump. The PD fluid pump may also be electromechanically driven gear, peristaltic or centrifugal pump. In a further alternative embodiment, a pneumatically driven PD fluid pump may be employed. Any of the above pumping scenarios may be used in combination with the electromechanically actuated solenoid valves of the present disclosure. The PD machine or cycler is in one embodiment capable of delivering fresh, heated PD fluid to the patient at, for example, 14 kPa (2.0 psig) or higher. The PD machine is capable of removing used PD fluid or effluent from the patient at, for example, −9 kPa (−1.3 psig) or an even greater negative pressure. Fresh PD fluid delivered to the patient may be first heated to a body fluid temperature, e.g., 37° C.

The PD machine or cycler also includes a plurality of valves, any one, or more, or all of which may be solenoid valves. The solenoid valves discussed herein may be of any variety or type. For example, one type of solenoid valve uses an internal fluid pathway that is either open or closed depending on whether the coil is energized. This type of solenoid valve is well suited for durable or reusable versions of the PD machine or cycler. Another type of solenoid valve operates by unclosing or closing a flexible tube depending on whether the coil is energized. This type of solenoid valve is well suited for versions of the PD machine or cycler operating with a disposable set but may also be used with a durable version of the PD machine or cycler, which would have internal flexible tubing for operating with the solenoid valves.

Noise Reduction

The PD machine or cycler of the present system operates with solenoid valves under control of a control unit. The control unit in various embodiments takes measures to control the movement of the solenoid valve to minimize the amount of sound that occurs at impact during activation and deactivation of the valve. The measures in general include the slowing of the movement of the valve plunger within the valve coil. Any modification that slows the movement of the valve will yield a smaller impact with the valve housing and generate a lower level of impact sound.

One structure and methodology for slowing solenoid valve actuation is to provide transistor ramping with the electronics for controlling the valves. Transistors may be used to linearly control the applied voltage to the coil of the solenoid valve. There are different variations of transistors that may be used for slowing solenoid valve actuation include NPN-transistors and metal oxide semiconductor field effect transistors ("MOSFET's"). The two different types of transistors have different capabilities and positive aspects.

The system of the present disclosure provides a control unit having one or more processor and one or more memory for controlling the solenoid valves of the present disclosure. For example, the control unit may provide electrical control for controlling an NPN-transistor using an ON/OFF signal. The control unit in one embodiment maintains the control signal at a low level, e.g., in the transistor's non-saturated zone, wherein the voltage applied to the solenoid coil is increased over time to by increasing input current to the transistor. The electrical outcome here is similar to that of a low pass filter without the need for a large capacitance or resistors placed in series with the solenoid. One downside of using NPN-transistors for slowing power applied to a solenoid valve coil is that the NPN-transistors have relatively high resistances that generate heat.

The control unit of the present disclosure may alternatively operate with one or more MOSFET, such as a P-Channel MOSFET. Here, the control unit provides a digital output control signal to the MOSFET. When the control signal from the control unit to a first MOSFET via the ramping electronics becomes high, the output signal from a second MOSFET increases over time until reaching a voltage Vin for a solenoid coil. When the control signal from the control unit to the first MOSFET is turned low (e.g., via associated electronics between the control unit and the first MOSFET ramping the control signal), the output voltage from the second MOSFET slowly ramps down to 0V. The time of the voltage up-ramping and down-ramping can be adjusted by changing the values of an associated capacitor. The ramping of the solenoid voltage due to the use of the MOSFET adds unwanted turn-on and turn-off delays to the control of the solenoid valve. To shorten the delays, an initial ramp offset may be added to the circuit. The offset value is set in one embodiment to a voltage that is near the lowest voltage that induces a movement of the valve plunger. The ramp offset voltage is set in one embodiment by adjusting a feedback resistor in the circuit. One benefit of using a MOSFET to slowly ramp on and ramp off the valve is that less electromagnetic interference ("EMI") is radiated and/or conducted since there are reoccurring and/or fast changing voltage flanks.

A further alternative structure and methodology for slowing solenoid valve actuation is to use Pulse Width Modulation ("PWM"). PWM has advantages over simply lowering the supply voltage in that a full voltage is eventually applied to the solenoid coil, which all but guarantees that the plunger of the solenoid valve is moved. In one embodiment, the control unit applies PWM by pulsing the input voltage ON/OFF and increasing the voltage over time until the plunger of the solenoid valve is moved to a valve open positon (two-way valve) or flow path switched position (three-way valve). Such pulsing and ramping allows for a slower movement of the plunger and thus a lesser impact with the valve housing upon activation and deactivation, reducing noise. PWM is also available during normal operation (e.g., steady state operation requiring less voltage), which allows the overall power demand during treatment to be lowered, keeping the PD machine or cycler cooler. For example, during a steady state operation, less voltage (e.g., 12 to 16 VDC) may be needed to hold the plunger in an open position, when compared to the voltage typically required for valve activation or valve deactivation (e.g., approximately 24 VDC). PWM applied during the steady state operation would accordingly result in lower power consumption.

In one PWM example, a master processor of the control unit provides an input/output driver of the control unit a command to energize one of the solenoid valves of the PD machine. The input/output driver sets the ON/OFF cycler for the PWM signal to the coil of the solenoid valve, e.g., zero to 100% every 50 milliseconds ("ms"). After the plunger of the solenoid valve has reached its end-of-travel position, the input/output driver cause the voltage level to be reduced, e.g., to 50% of the final actuation power level (e.g., to maintain the valve energized in an open position), reducing power consumption and heat generation. When it is time to close a two-way valve or switch the flowpaths of a three-way valve, the I/O driver causes the PWM voltage level to drop from the plunger hold level of 50% to zero, e.g., over 50 ms.

The duration of the ramping up or ramping down of voltage applied to the solenoid coil of a valve may be adjusted for any of the methodologies for noise reduction described herein. For example, resistors and/or capacitors may be arranged between a control unit and one of the NPN transistor, the MOSFET, or the I/O node associated with the valve. The resistance values and/or the capacitance values may be selected to accordingly set the duration of the ramp up and/or ramp down.

Assessing the Functionality of Solenoid Valve Activation

As discussed herein, solenoid valves generally open by energizing a coil that moves a plunger within a housing of the solenoid valve (e.g., as in a solenoid plunger valve) and/or releases a pinched status of a tube (e.g., as in a solenoid pinch valve). However, there is a desire and need to assess whether the solenoid valve of a medical fluid machine or cycler (e.g., a PD, an HD, an HF, an HDF, and/or a CRRT machine or cycler) has actually opened when energized or has actually closed when de-energized or deactivated. If not, a situation may occur where dialysis fluid is not flowing when it is supposed to be flowing, or where dialysis fluid is flowing when it is supposed to not be flowing. Various embodiments of systems and methods of the present disclosure are provided for assessing valve activation (e.g., whether a valve has opened correctly) or valve deactivation (e.g., whether a valve has actually closed). In at least one embodiment, measurements of current values may be received from a solenoid valve at a predetermined sampling rate over a predetermine duration of time to generate a current profile for the solenoid valve. An, e.g., fifth degree, polynomial model may be fit to the current profile and optimized. The optimized polynomial model may be applied to a trained classification model (e.g., a trained support vector machine ("SVM")) to determine whether the current profile indicates that the corresponding solenoid valve has actually opened or closed.

A trained classification model, such as a trained SVM, may comprise a supervised learning model that analyzes training data (e.g., a plurality of current profiles used as a reference (referred to herein as reference current profiles), and knowledge of whether each reference current profile corresponds to a successful activation or a failed activation) to automatically learn (e.g., via an iterative error minimization process) relationships between an input data (e.g., various parameters of any given current profile) and two or more discrete outcomes (e.g., whether the current profile corresponds to a successful activation or a failed activation). The learned relationship can then be applied to testing data with an unknown outcome (e.g., a current profile for a valve for which the valve activation state is not known) to determine the outcome (e.g., whether the valve has actually undergone a successful activation). An SVM may be an example of a classification model in which the learned relationship is a decision boundary (e.g., to separate current profiles of valves with successful valve activations from current profiles of valves with failed valve activations).

In light of the disclosure set forth herein, and without limiting the disclosure in any way, in a first aspect of the present disclosure, which may be combined with any other aspect, or portion thereof, a medical fluid system includes a control unit: a plurality of NPN transistors configured to control a plurality of valves, in response to control signals received from the control unit: a plurality of valves, wherein each valve comprises a housing, a coil, and a plunger, and wherein each valve is configured to allow a flow of medical fluid through a tube by applying, via an associated NPN transistor, voltage to the corresponding coil to move the corresponding plunger within the corresponding housing: and wherein the control unit comprises at least one processor and at least one memory, wherein the at least one memory stores instructions that, when executed by the at least one processor, causes the at least one processor to: transmit, to one of the NPN transistors, a control signal configured to cause a ramping up of input current to the NPN transistor, wherein the ramping up of the input current to the NPN transistor causes a corresponding valve to ramp up the voltage applied to the corresponding coil, and wherein the ramping up of the voltage applied to the corresponding coil causes the corresponding plunger to move in a manner in which sound generated by the corresponding plunger is reduced in comparison to operation without the NPN transistor.

In a second aspect of the present disclosure, which may be combined with any other aspect, or portion thereof, the control signal is configured to place the NPN transistor in a non-saturated zone.

In a third aspect of the present disclosure, which may be combined with any other aspect, or portion thereof, each valve is configured to close the flow of medical fluid through the tube by un-applying, as caused by the corresponding NPN transistor, the voltage to the corresponding coil so that the corresponding plunger moves in an opposite direction to occlude the corresponding tube.

In a fourth aspect of the present disclosure, which may be combined with any other aspect, or portion thereof, the instructions, when executed by the at least one processor, further cause the at least one processor to: turn off the low control signal, wherein the turning off causes a ramping down of the input current to the NPN transistor, wherein the ramping down of the input current to the NPN transistor causes the corresponding valve to ramp down the voltage applied to the corresponding coil, and wherein the ramping down of the voltage applied to the corresponding coil causes the corresponding plunger to move in an opposite direction and in a manner in which sound generated by the corresponding plunger is reduced in comparison to operation without the NPN transistor.

In a fifth aspect of the present disclosure, which may be combined with any other aspect, or portion thereof, a medical fluid system includes a control unit: a plurality of metal oxide semiconductor field effect transistors ("MOSFETs") configured to control a plurality of valves, in response to control signals received from the control unit: a plurality of valves, wherein each valve comprises a housing, a coil, and a plunger, and wherein each valve is configured to allow a flow of medical fluid through a tube by applying, via an associated MOSFET, voltage to the corresponding coil to move the corresponding plunger within the corresponding housing: the control unit comprising at least one processor and at least one memory, wherein the at least one memory stores instructions that, when executed by the at least one processor, causes the at least one processor to: transmit, to one of the MOSFETs, a high digital control signal, wherein the MOSFET, responsive to the high digital control signal, causes a corresponding valve to ramp up the voltage applied to a corresponding coil until the voltage reaches a predetermined input voltage. Vin, and wherein the ramping up of the voltage applied to the corresponding coil causes the corresponding plunger to move in a manner in which sound generated by the corresponding plunger is reduced in comparison to operation without the MOSFET.

In a sixth aspect of the present disclosure, which may be combined with any other aspect, or portion thereof, each valve is configured to close the flow of medical fluid through the tube by un-applying, via the corresponding MOSFET, the voltage to the corresponding coil so that the corresponding plunger moves in an opposite direction to occlude the corresponding tube.

In a seventh aspect of the present disclosure, which may be combined with any other aspect, or portion thereof, the instructions, when executed by the at least one processor, further causes the at least one processor to: transmit, to the MOSFET of the plurality of MOSFETs, a low digital control signal wherein the MOSFET, responsive to the low digital control signal, causes the corresponding valve to ramp down the voltage applied to the corresponding coil until the voltage reaches 0 volts, and wherein the ramping down of the voltage applied to the corresponding coil causes the corresponding plunger to move in an opposite direction and in a manner in which sound generated by the corresponding plunger is reduced in comparison to operation without the MOSFET.

In an eighth aspect of the present disclosure, which may be combined with any other aspect, or portion thereof, the medical fluid system further includes at least one resistor serially arranged between the control unit and the MOSFET: wherein a duration of the ramping up of the voltage applied to the corresponding coil is based on at least one resistance value of the corresponding at least one resistor; and wherein a duration of the ramping down of the voltage applied to the corresponding coil is based on the at least one resistance value of the corresponding at least one resistor.

In a ninth aspect of the present disclosure, which may be combined with any other aspect, or portion thereof, the medical fluid system further includes at least one capacitor serially arranged between the control unit and the MOSFET: wherein the duration of the ramping up of the voltage applied to the corresponding coil is further based on capacitance values of the corresponding at least one capacitor: and wherein the duration of the ramping down of the voltage applied to the corresponding coil is further based on the capacitance values of the corresponding at least one capacitor.

In a tenth aspect of the present disclosure, which may be combined with any other aspect, or portion thereof, the medical fluid system further includes an initial ramp offset circuit comprising a feedback resistor.

In an eleventh aspect of the present disclosure, which may be combined with any other aspect, or portion thereof, the instructions, when executed, further cause the processor to: apply, via the initial ramp offset circuit, an offset voltage set below the voltage applied to the corresponding coil when ramping up the input current to the MOSFET.

In a twelfth aspect of the present disclosure, which may be combined with any other aspect, or portion thereof, a medical fluid system includes a control unit: a plurality of input/output ("I/O") nodes configured to control a plurality of valves via pulse width modulation ("PWM") signals, in response to control signals received from the control unit: a plurality of valves, wherein each valve comprises a housing, a coil, and a plunger, and wherein each valve is configured to allow a flow of medical fluid through a tube by applying, via an associated I/O node, voltage to the corresponding coil to move the corresponding plunger within the corresponding housing: and the control unit comprising at least one processor and at least one memory, wherein the at least one memory stores instructions that, when executed by the at least one processor, causes the at least one to: transmit, to an I/O node of the plurality of I/O nodes, a control signal causing the I/O node to apply and ramp up a PWM signal to the corresponding coil, and wherein the ramping up of the PWM signal causes the corresponding plunger to move in a manner in which sound generated by the corresponding plunger is reduced in comparison to operation without the PWM signal.

In a thirteenth aspect of the present disclosure, which may be combined with any other aspect, or portion thereof, ramping up of the PWM signal comprises ramping up a duty cycle of a pulsed application of voltage to the corresponding coil from 0% to 100% during 50 ms.

In a fourteenth aspect of the present disclosure, which may be combined with any other aspect, or portion thereof, the instructions, when executed, further cause the processor to: after the plunger reaches the end position, transmit, to the I/O node, a second control signal causing the I/O node to ramp down the PWM signal to the corresponding coil to a duty cycle that is at least 25%.

In a fifteenth aspect of the present disclosure, which may be combined with any other aspect, or portion thereof, the second control signal causes the I/O node to ramp down the PWM signal to the corresponding coil to a duty cycle that is at least 50%.

In a sixteenth aspect of the present disclosure, which may be combined with any other aspect, or portion thereof, each valve is configured to close the flow of medical fluid through the tube by un-applying, via the corresponding I/O node, the voltage to the corresponding coil so that the corresponding plunger moves in an opposite direction to occlude the corresponding tube.

In a seventeenth aspect of the present disclosure, which may be combined with any other aspect, or portion thereof, the instructions, when executed by the at least one processor, further causes the at least one processor to: transmit, to the I/O node, a third control signal causing the I/O node to ramp down the PWM signal to the corresponding coil to a duty cycle of 0%, wherein the ramping down of the PWM signal to the corresponding coil causes the corresponding plunger to move in an opposite direction and in manner in which sound generated by the corresponding plunger is reduced in comparison to operation without the PWM signal.

In an eighteenth aspect of the present disclosure, which may be combined with any other aspect, or portion thereof, ramping down the PWM signal to the corresponding coil to the duty cycle of 0% occurs in between 25 to 75 ms.

In a nineteenth aspect of the present disclosure, which may be combined with any other aspect, or portion thereof, the medical fluid system further includes at least one resistor serially arranged between the control unit and the I/O node: wherein a duration of the ramping up of the PWM signal is based on resistance values of the corresponding at least one resistor; and wherein a duration of the ramping down of the PWM signal is based on the resistance values of the corresponding at least one resistor.

In a twentieth aspect of the present disclosure, which may be combined with any other aspect, or portion thereof, the medical fluid system further includes at least one capacitor serially arranged between the control unit and the I/O node: wherein the duration of the ramping up of the PWM signal is further based on capacitance values of the corresponding at least one capacitor: and wherein the duration of the ramping down of the PWM signal is further based on the capacitance values of the corresponding at least one capacitor.

In a twenty-first aspect of the present disclosure, which may be combined with any other aspect, or portion thereof, a medical fluid system includes a plurality of valves, wherein each valve comprises a housing, a coil, and a plunger, wherein each valve is configured to allow a flow of medical fluid through a tube by energizing the corresponding coil to move the corresponding plunger within the corresponding housing, and wherein each valve is configured to close the flow of medical fluid through the tube by de-energizing the corresponding coil to move the corresponding plunger in an opposite direction within the corresponding housing to occlude the corresponding tube: at least one processor: and at least one memory storing instructions that, when executed by the at least one processor, cause the at least one processor to: receive, during activation of at least one of the plurality of valves, measured current values at a predetermined sampling rate over a predetermined duration, generate, based on the respective measured current values for the at least one valve, a current profile for the at least one valve, generate, based on the respective current profile for the at least one valve, a polynomial model for the at least one valve, and apply, for the at least one valve, the respective polynomial model to a trained classification model to assess an activation status for the valve.

In a twenty-second aspect of the present disclosure, which may be combined with any other aspect, or portion thereof, the activation status indicates one of a successful activation or a failed activation, wherein the instructions, when executed, further cause the system to: generate, based on the activation status indicating the failed activation, an alert indicating a malfunction of a valve associated with the failed activation.

In a twenty-third first aspect of the present disclosure, which may be combined with any other aspect, or portion thereof, the instructions, when executed, cause the system to generate the polynomial model by: applying, to the current profile of the at least one valve, a fifth degree polynomial model having initialized parameters: and optimizing, via least mean square estimation, parameters of the fifth degree polynomial model.

In a twenty-fourth aspect of the present disclosure, which may be combined with any other aspect, or portion thereof, the instructions, when executed, cause the system to generate the current profile for the at least one valve by: normalizing, using a maximum current value, the measured current values for the at least one valve.

In a twenty-fifth aspect of the present disclosure, which may be combined with any other aspect, or portion thereof, the instructions, when executed, cause the system to normalize the measured current values by: identifying, based on the measured current values of the at least one valve, a current risetime for the at least one valve; and determining, based on the current risetime for the at least one valve, a maximum current for the normalization of measured current values for the at least one valve.

In a twenty-sixth aspect of the present disclosure, which may be combined with any other aspect, or portion thereof, the trained classification model is one or more of: a support vector machine trained using a reference dataset comprising a plurality of reference current profiles having known activation statuses: or a logistic regression model trained using the reference dataset comprising the plurality of reference current profiles having known activation statuses.

In a twenty-seventh aspect of the present disclosure, which may be combined with any other aspect, or portion thereof, the instructions, when executed, further cause the system to, prior to applying the respective polynomial model to the trained classification model, receive a first reference dataset comprising a plurality of reference current profiles indicating a successful activation: receive a second reference dataset comprising a plurality of reference current profiles indicating a failed activation: label the first reference dataset and the second reference data set with a positive output and a negative output, respectively: iteratively test one or more decision boundaries separating the first reference dataset and the second reference dataset: and generate, after convergence based on an optimized decision boundary, the trained classification model.

In a twenty-eighth aspect of the present disclosure, which may be combined with any other aspect, or portion thereof, a medical fluid system includes a plurality of valves, wherein each valve comprises a housing, a coil, and a plunger, wherein each valve is configured to allow a flow of medical fluid through a tube by energizing the corresponding coil to move the corresponding plunger within the corresponding housing, and wherein each valve is configured to close the flow of medical fluid through the tube by de-energizing the corresponding coil to move the corresponding plunger in an opposite direction within the corresponding housing to occlude the corresponding tube: at least one processor: and at least one memory storing instructions that, when executed by the at least one processor, cause the at least one processor to: receive, during deactivation of at least one of the plurality of valves, measured current values at a predetermined sampling rate over a predetermined duration, generate, based on the respective measured current values for the at least one valve, a current profile for the at least one valve, generate, based on the respective current profile for the at least one valve, a polynomial model for the at least one valve, and apply, for the at least one valve, the respective polynomial model to a trained classification model to assess a deactivation status for the at least one valve.

In a twenty-ninth aspect of the present disclosure, which may be combined with any other aspect, or portion thereof, the deactivation status indicates one of a successful deactivation or a failed deactivation, wherein the instructions, when executed, further cause the system to: generate, based on the deactivation status indicating the failed deactivation, an alert indicating a malfunction of a valve associated with the failed deactivation.

In a thirtieth aspect of the present disclosure, which may be combined with any other aspect, or portion thereof, a method for assessing the functionality of a solenoid valve activation, the method comprising: receiving, by a control unit of a medical fluid system having at least one processor, and during activation of at least one of a plurality of valves controlled by the control unit, measured current values at a predetermined sampling rate over a predetermined duration, wherein each valve comprises a housing, a coil, and a plunger, wherein each valve is configured to activate a flow of medical fluid through a tube by energizing the corresponding coil to move the corresponding plunger within the corresponding housing, and wherein each valve is configured to close the flow of medical fluid through the tube by de-energizing the corresponding coil to move the corresponding plunger in an opposite direction within the corresponding housing to occlude the corresponding tube: generating, based on the respective measured current values for the at least one valve, a current profile for the at least one valve: generating, based on the respective current profile for the at least one valve, a polynomial model for the at least one valve: and applying, for the at least one valve, the respective polynomial model to a trained classification model to assess an activation status for the valve.

In a thirty-first aspect of the present disclosure, which may be combined with any other aspect, or portion thereof, the activation status indicates one of a successful activation or a failed activation, the method further comprising: generating, based on the activation status indicating a failed activation, an alert indicating a malfunction of a valve associated with the failed activation.

In a thirty-second aspect of the present disclosure, which may be combined with any other aspect, or portion thereof, generating the polynomial model comprises: applying, to the current profile of the at least one valve, a fifth degree polynomial model having initialized parameters: and optimizing, via least mean square estimation, parameters of the fifth degree polynomial model.

In a thirty-third aspect of the present disclosure, which may be combined with any other aspect, or portion thereof, generating the current profile for the at least one valve comprises: normalizing, using a maximum current value, the measured current values for the at least one valve.

In a thirty-fourth aspect of the present disclosure, which may be combined with any other aspect, or portion thereof, normalizing the measured current values for the at least one valve comprises: identifying, based on the measured current values of the at least one valve, a current risetime for the at least one valve: and determining, based on the current risetime for the at least one valve, a maximum current for the normalization of measured current values for the at least one valve.

In a thirty-fifth aspect of the present disclosure, which may be combined with any other aspect, or portion thereof, the trained classification model is one or more of: a support vector machine trained using a reference dataset comprising a plurality of reference current profiles having known activation statuses: or a logistic regression model trained using the reference dataset comprising the plurality of reference current profiles having known activation statuses.

In a thirty-sixth aspect of the present disclosure, which may be combined with any other aspect, or portion thereof, the method further comprises, prior to applying the respective polynomial model to the trained classification model: receiving a first reference dataset comprising a plurality of reference current profiles indicating a successful activation; receiving a second reference dataset comprising a plurality of reference current profiles indicating a failed activation: labeling the first reference dataset and the second reference data set with a positive output and a negative output, respectively: iteratively testing one or more decision boundaries separating the first reference dataset and the second reference dataset: and generating, after convergence based on an optimized decision boundary, the trained classification model.

In a thirty-seventh aspect of the present disclosure, which may be combined with any other aspect, or portion thereof, a method for assessing the functionality of a solenoid valve deactivation includes receiving, by a control unit of a medical fluid system having at least one processor, and during deactivation of at least one of a plurality of valves controlled by the control unit, measured current values at a predetermined sampling rate over a predetermined duration, wherein each valve comprises a housing, a coil, and a plunger, wherein each valve is configured to activate a flow of medical fluid through a tube by energizing the corresponding coil to move the corresponding plunger within the corresponding housing, and wherein each valve is configured to close the flow of medical fluid through the tube by de-energizing the corresponding coil to move the corresponding plunger in an opposite direction within the corresponding housing to occlude the corresponding tube; generating, based on the respective measured current values for the at least one valve, a current profile for the at least one valve; generating, based on the respective current profile for the at least one valve, a polynomial model for the at least one valve: and applying, for the at least one valve, the respective polynomial model to a trained classification model to assess a deactivation status for the valve.

In a thirty-eighth aspect of the present disclosure, which may be combined with any other aspect, or portion thereof, the deactivation status indicates one of a successful deactivation or a failed deactivation, the method further comprising: generating, based on the deactivation status indicating the failed deactivation, an alert indicating a malfunction of a valve associated with the failed deactivation.

In a thirty-ninth aspect of the present disclosure, which may be combined with any other aspect, or portion thereof, one or more non-transitory computer readable medium storing instructions that, when executed by at least one processor, cause the at least one processor to: receive, during activation of at least one of a plurality of valves controlled by a control unit of a medical fluid system, measured current values at a predetermined sampling rate over a predetermined duration, wherein each valve comprises a corresponding housing, a corresponding coil, and a corresponding plunger, wherein each valve is configured to activate a flow of medical fluid through a tube by energizing the corresponding coil to move the corresponding plunger within the corresponding housing, wherein each valve is configured to close the flow of medical fluid through the tube by de-energizing the corresponding coil to move the corresponding plunger in an opposite direction within the corresponding housing to occlude the corresponding tube: generate, based on the respective measured current values for the at least one valve, a current profile for the at least one valve: generate, based on the respective current profile for the at least one valve, a polynomial model for the at least one valve: and apply, for the at least one valve, the respective polynomial model to a trained classification model to assess an activation status for the at least one valve.

In a fortieth aspect of the present disclosure, which may be combined with any other aspect, or portion thereof, the activation status indicates one of a successful activation or a failed activation, the non-transitory computer readable medium further configured to: generate, based on the activation status indicating a failed activation, an alert indicating a malfunction of a valve associated with the failed activation.

In a forty-first aspect of the present disclosure, which may be combined with any other aspect, or portion thereof, any of the features, functionality and alternatives described in connection with any one or more of FIGS. 1 to 14 may be combined with any of the features, functionality and alternatives described in connection with any other of FIGS. 1 to 14.

In light of the above aspects and present disclosure set forth herein, it is an advantage of the present disclosure to provide a medical fluid system having improved solenoid valve operation.

It is another advantage of the present disclosure to provide a medical fluid system having solenoid valve methodology that reduces noise created by valve operation.

It is a further advantage of the present disclosure to provide a medical fluid system having solenoid valve methodology that reduces noise without the need for additional equipment.

It is yet another advantage of the present disclosure to provide a medical fluid system having solenoid valve methodology that ensures proper opening and closing of the solenoid valves.

It is yet a further advantage of the present disclosure to provide a medical fluid system having solenoid valve methodology that ensures proper opening and closing of the solenoid valves without the need for additional equipment.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

System Overview

Figure 1:
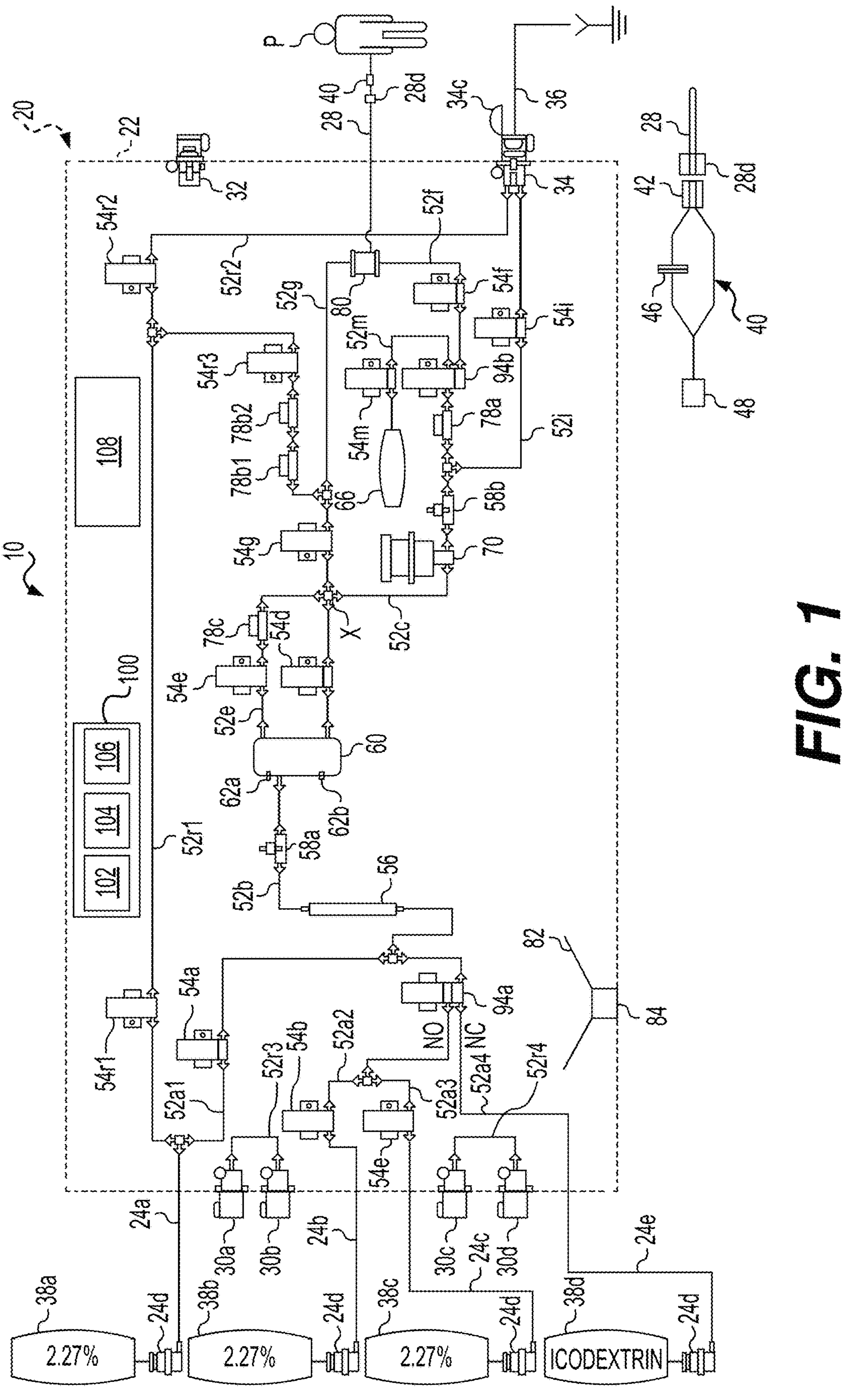
FIG. 1 is a sectioned schematic view of one embodiment for an automated PD system having the solenoid valve operation of the present disclosure.

Referring now to the drawings and in particular to FIG. 1, an example system 10 including the solenoid valve operation of the present disclosure is illustrated. System 10 includes a dialysis machine 20, such as an automated peritoneal dialysis ("PD") machine, and a control unit 100 having one or more processor 102, one or more memory 104, video controller 106 and user interface 108. Control unit 100 controls all electrical fluid flow and heating components of system 10 and receives outputs from all sensors of system 10. System 10 in the illustrated embodiment includes durable and reusable components that contact medical fluid, such as PD fluid, which necessitates that PD machine or cycler 20 be disinfected between treatments, e.g., via heat disinfection.

System 10 in FIG. 1 includes an inline resistive heater 56, reusable supply lines or tubes **52*al* to 52*a*4 and 52*b*, air trap 60 operating with respective upper and lower level sensors 62*a* and 62*b*, air trap valve 54*d*, vent valve 54*e* located along vent line 52*e*, reusable line or tubing 52*c*, dialysis fluid pump 70, temperature sensors 58*a* and 58*b*, pressure sensors 78*a*, 78*b*1, 78*b*2 and 78*c*, reusable patient tubing or lines 52*f* and 52*g* having respective valves 54*f* and 54*g*, dual lumen reusable patient line 28, hose reel 80 for retracting patient line 28, reusable drain tubing or line 52*i* extending to drain line connector 34 and having a drain line valve 54*i*, and reusable recirculation disinfection tubing or lines 52*rl* and 52*r*2 operating with respective disinfection valves 54*rl* and 54*r*2. A third recirculation or disinfection tubing or line 52*r*3 extends between disinfection connectors 30*a* and 30*b* for use during disinfection. A fourth recirculation or disinfection tubing or line 52*r*4 extends between disinfection connectors 30*c* and 30*d*** for use during disinfection.

System 10 further includes PD fluid containers or bags **38*a* to 38*c* (e.g., holding the same or different formulations of PD fluid), which connect to distal ends 24*d* of reusable PD fluid lines 24*a* to 24*c*, respectively. System 10*d* further includes a fourth PD fluid container or bag 38*d* that connects to a distal end 24*d* of reusable PD fluid line 24*e*. Fourth PD fluid container or bag 38*d* may hold the same or different type (e.g., icodextrin) of PD fluid than provided in PD fluid containers or bags 38*a* to 38*c*. Reusable PD fluid lines 24*a* to 24*c* and 24*e* extend in one embodiment through apertures (not illustrated) defined or provided by housing 22 of cycler 20**.

System 10 in the illustrated embodiment includes four disinfection connectors **30*a* to 30*d* for connecting to distal ends 24*d* of reusable PD fluid lines 24*a* to 24*c* and 24*e*, respectively, during disinfection. System 10 also provides patient line connector 32 that includes an internal lumen, e.g., a U-shaped lumen, which directs fresh or used dialysis fluid from one PD fluid lumen of dual lumen reusable patient line 28 into the other PD fluid lumen. Reusable supply tubing or lines 52*al* to 52*a*4 communicate with reusable supply lines 24*a* to 24*c* and 24*e*, respectively. Reusable supply tubing or lines 52*al* to 52*a*3 operate with valves 54*a* to 54*c*, respectively, to allow PD fluid from a desired PD fluid container or bag 38*a* to 38*c* to be pulled into cycler 20. Three-way valve 94*a* in the illustrated example allows for control unit 100 to select between (i) 2.27% (or other) glucose dialysis fluid from container or bag 38*b* or 38*c* and (ii) icodextrin from container or bag 38*d*. In the illustrated embodiment, icodextrin from container or bag 38*d* is connected to the normally closed port of three-way valve 94*a***.

FIG. 1 also illustrates that system 10 includes and uses disposable filter set 40, which communicates fluidly with the fresh and used PD fluid lumens of dual lumen reusable patient line 28. Disposable filter set 40 includes a disposable connector 42 that connects to distal end **28*d* of reusable patient line 28. Disposable filter set 40 includes a connector 48 that connects to the patient's transfer set. Disposable filter set 40 further includes a sterilizing grade filter membrane 46** that further filters fresh PD fluid.

System 10 is constructed in one embodiment such that drain line **52*i* during filling is fluidly connected downstream from dialysis fluid pump 70. In this manner, if drain valve 54*i* fails or somehow leaks during a patient fill of patient P, fresh PD fluid is pushed down disposable drain line 36 instead of used PD fluid potentially being pulled into pump 70. Disposable drain line 36 is in one embodiment removed for disinfection, while drain line connector 34 is capped via a cap 34*c***.

System 10 further includes a leak detection pan 82 located at the bottom of housing 22 of cycler 20 and a corresponding leak detection sensor 84 outputting to control unit 100. In the illustrated example, system 10 is provided with an additional pressure sensor **78*c* located upstream of dialysis fluid pump 70, which allows for the measurement of the suction pressure of pump 70 to help control unit 100 to more accurately determine pump volume. Additional pressure sensor 78*c* in the illustrated embodiment is located along vent line 52*e*, which may be filled with air or a mixture of air and PD fluid, but which should nevertheless be at the same negative pressure as PD fluid located within PD fluid line 52*c***.

System 10 in the example of FIG. 1 includes redundant pressure sensors **78*b*1 and 78*b*2, the output of one of which is used for pump control, as discussed herein, while the output of the other pressure sensor is a safety or watchdog output to make sure the control pressure sensor is reading accurately. Pressure sensors 78*b*1 and 78*b*2 are located along a line including a third recirculation valve 54*r*3. In still a further example, system 10 may employ one or more cross, marked via an X in FIG. 1**, which may (i) reduce the overall amount and volume of the internal, reusable tubing. (ii) reduce the number of valves needed, and (iii) allow the portion of the fluid circuitry shared by both fresh and used PD fluid to be minimized.

System 10 in the example of FIG. 1 further includes a source of acid, such as a citric acid container or bag 66. Citric acid container or bag 66 is in selective fluid communication with second three-way valve **94*b* via a citric acid valve 54*m* located along a citric acid line 52*m*. Citric acid line 52*m* is connected in one embodiment to the normally closed port of second three-way valve 94*b*, so as to provide redundant valves between citric acid container or bag 66** and the PD fluid circuit during treatment. The redundant valves ensure that no citric (or other) acid reaches the treatment fluid lines during treatment. Citric (or other) acid is instead used during disinfection.

It should be appreciated that system 10 is not required to (i) be a dialysis system, or (ii) use redundant or durable components that are disinfected between uses to employ the sensor thermoelectric heating of the present disclosure.

System 10 may instead be any type of medical fluid system and may employ a disposable set having a disposable pumping portion that contacts the corresponding medical fluid. In the primary example described herein, the solenoid valves are described as operating with PD machine or cycler 20.

Any one or more or all of valves 54*a* to 54*h*, 54*m*, and 54*r*1 to 54*r*4, 94*a* and 94*b* may be a solenoid valve, which may be of a type of that uses an internal fluid pathway that is either open or closed depending on whether the coil is energized. This type of solenoid valve is well suited for durable or reusable versions of the PD machine or cycler. Another type of solenoid valve for valves 54*a* to 54*h*, 54*m*, and 54*r*1 to 54*r*4 operates by unclosing or closing a flexible tube depending on whether the coil is energized. This type of solenoid valve is well suited for versions of the PD machine or cycler operating with a disposable set but may also be used with a durable version of the PD machine or cycler, which would have internal flexible tubing for operating with the solenoid valves.

Figure 2:
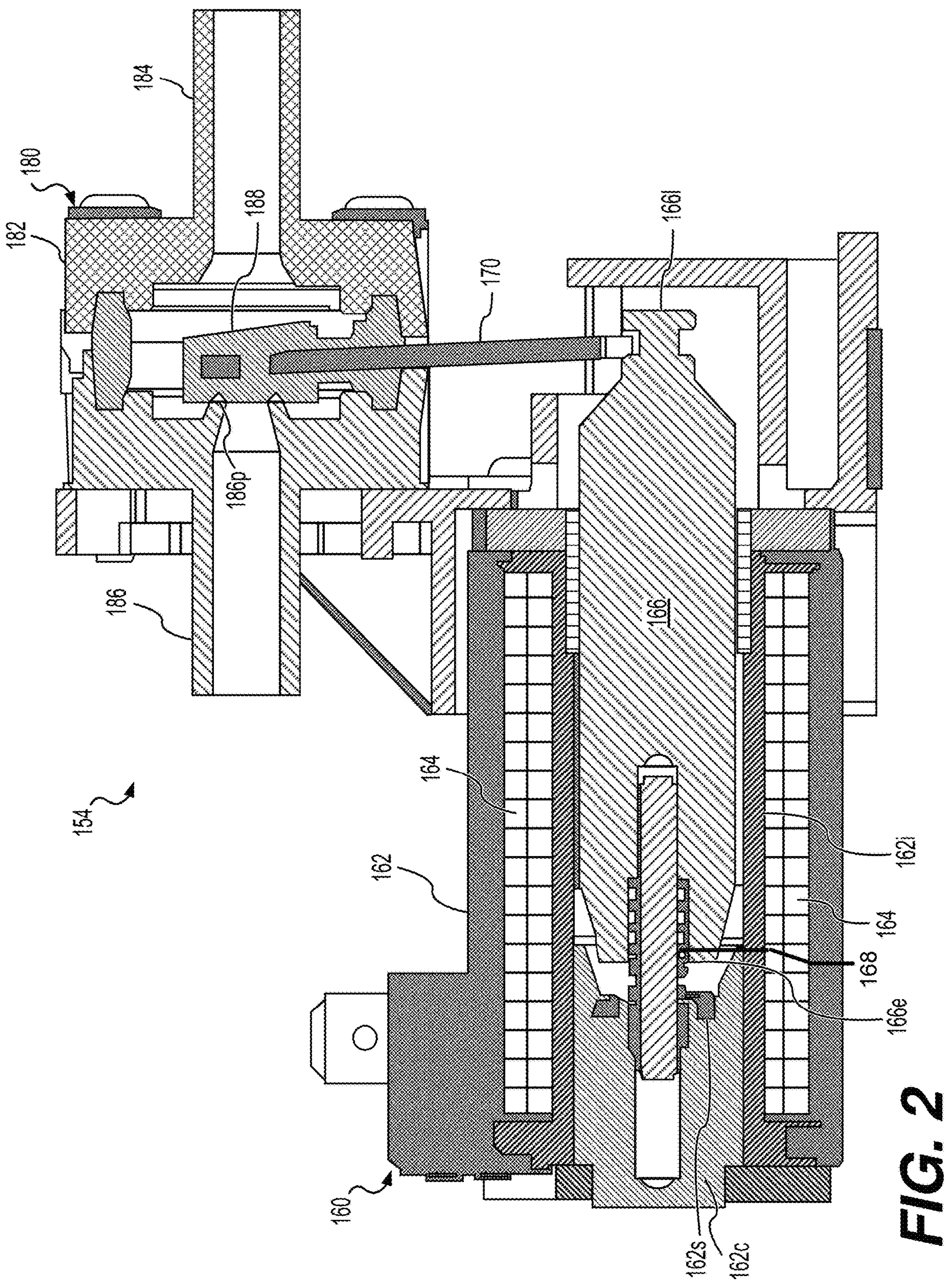
FIG. 2 is a sectioned elevation view of one embodiment for a two-way valve useable with the systems and associated methodology of the present disclosure.

Referring now to FIG. 2, one suitable two-way solenoid valve 154 for two-way valves 54*a* to 54*h*, 54*m*, and 54*r*1 to 54*r*4 is illustrated. Valve 154 of FIG. 2 is of a type of that uses an internal fluid pathway that is either open or closed depending on whether the coil is energized. Valve 154 includes two primary sections, namely, a solenoid section 160 and a valve section 180. Solenoid section 160 includes a solenoid housing 162. Solenoid housing 162 supports a coil 164, which extends around an inner wall 162*i* of housing 162, and which is energized to move or translate a solenoid plunger 166. A compression spring 168 is provided and is positioned so as to bias plunger 166 into a closed position when energy is removed from coil 164.

FIG. 2 illustrates that plunger 166 has a contacting end 166*e*. Also, a core portion 162*c* of solenoid housing 162 is provided with a stop 162*s*. When coil 164 is energized, a magnetic field is induced, causing solenoid plunger 166 to translate within the inner wall 162*i* of housing 162 from right to left, such that contacting end 166*e* of plunger 166 abuts stop 162*s* to provide an end-of-travel for plunger 166 in a valve open position. The abutting contact of end 166*e* with stop 162*s* causes noise, which may become problematic for the PD patient especially if the patient is trying to sleep. Described herein is structure and associated methodology to help reduce the noises cause by the abutting contact of end 166*e* with stop 162*s*.

FIG. 2 illustrates two-way solenoid valve 154 in a closed or no fluid flow condition. Here, coil 164 is not energized, such that compression spring 168 pushes contacting end 166*e* of plunger 166 away from the stop 162*s* provided at core portion 162*c* of solenoid housing 162. A lever end 1661 of plunger 166 is translated such that a lever 170 held rotatably at the lever end 1661 of plunger 166 is tilted so as to close a fluid pathway located within valve section 180 of valve 154.

Valve section 180 of valve 154 includes a valve housing 182. Valve housing 182 defines a fluid inlet 184 and a fluid outlet 186. The portion of lever 170 extending into valve housing 182 is fitted with a membrane or stopper 188, which may be made of a medically safe compressible (sealable) rubber, such as silicone. In the closed position of FIG. 2, where coil 164 is not energized and compression spring 168 is extended, lever 170 pivots membrane or stopper 188 so as to contact and seal closed an inner, e.g., beveled port 186*p* of outlet 186, preventing fluid flow. When coil 164 is energized, plunger 166 moves to the left so as to compress spring 168 and pivot lever 170, such that membrane or stopper 188 moves away from beveled port 186*p* of outlet 186 and stops at a substantially vertical position. Here, fluid, such as water or PD fluid is able to flow from fluid inlet 184, around membrane or stopper 188, and through fluid outlet 186.

When valve 154 is closed and membrane or stopper 188 is sealed against beveled port 186*p* of fluid outlet 186, the fluid pressure downstream from outlet 186 is less than the fluid pressure upstream of fluid inlet 184. The pressure delta helps to seal membrane or stopper 188 against beveled port 186*p*, such that compression spring 168 does not need to supply a force needed (or all of the force needed) to keep the membrane or stopper sealed against the beveled port. The main function of compression spring 168 is to translate plunger 166 when coil 164 is de-energized. It should be appreciated however that the pressure delta that helps to seal membrane or stopper 188 against beveled port 186*p* when valve 154 is to be closed, also fights against the magnetic force induced when coil 164 is energized. Described herein is structure and associated functionality for ensuring that valve 154 is properly opened when it is supposed to be.

Figure 3:
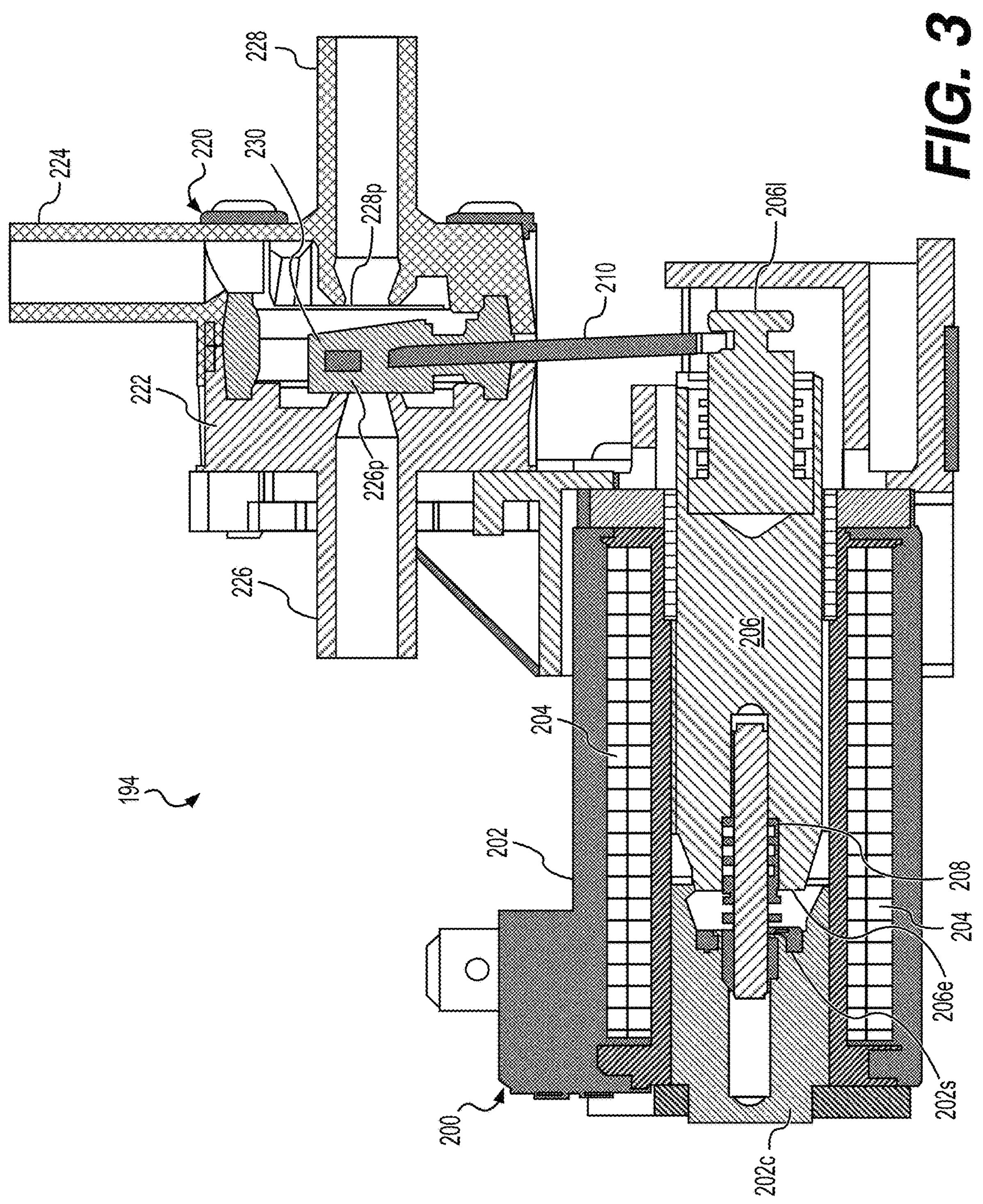
FIG. 3 is a sectioned elevation view of one embodiment for a three-way valve useable with the systems and associated methodology of the present disclosure.

Referring now to FIG. 3, one suitable three-way solenoid valve 194 for three-way valves 94*a*, 94*b* is illustrated. Valve 194 of FIG. 3 is of a type of that uses an internal fluid pathway that is either open or closed depending on whether the coil is energized. Valve 194, like valve 154, includes two primary sections, namely, a solenoid section 200 and a valve section 220. Solenoid section 200 is basically the same as solenoid section 160 of valve 154. Solenoid section includes a solenoid housing 202 that supports a coil 204, which is energized to move or translate a solenoid plunger 206. A compression spring 208 is provided and is positioned so as to bias plunger 206 into a closed position when energy is removed from coil 164. Plunger 206 has a contacting end 206*e*, which abuts a stop 202*s* provides at a core portion 202*c* of solenoid housing 202 when coil 204 is energized. The abutting contact of end 206*e* with stop 202*s* causes noise, which may become problematic for the PD patient especially if the patient is trying to sleep. Described herein is structure and associated methodology to help reduce the noises cause by the abutting contact of end 206*e* with stop 202*s*.

FIG. 3 illustrates three-way solenoid valve 194 in a normally closed condition. Here, coil 204 is not energized, such that compression spring 208 pushes contacting end 206*e* of plunger 206 away from the stop 202*s* provided at core portion 202*c* of solenoid housing 202. A lever end 2061 of plunger 206 is translated such that a lever 210 held rotatably at the lever end 2061 of plunger 206 is tilted so as to close a fluid pathway located within valve section 220 of valve 194.

Valve section 220 is where three-way valve 194 differs from two-way valve 154. Valve section 220 includes a valve housing 222 defining a fluid inlet 224, a normally closed fluid outlet 226 and a normally open fluid outlet 228. The portion of lever 210 extending into valve housing 222 is fitted with a membrane or stopper 230, which may again be made of a medically safe compressible (sealable) rubber, such as silicone. In the normally closed position of FIG. 2, where coil 204 is not energized and compression spring 208 is extended, lever 210 pivots membrane or stopper 230) so as to contact and seal closed an inner, e.g., beveled, port 226*p* of normally closed fluid outlet 226, preventing fluid flow through the normally closed outlet. When coil 204 is energized, plunger 206 moves to the left so as to compress spring 208 and pivot lever 210, such that membrane or stopper 230 moves away from beveled port 226*p* of normally closed fluid outlet 226 to instead contact and seal closed an inner, e.g., beveled, port 228*p* of normally open fluid outlet 228, preventing fluid flow through the normally open outlet. In the normally closed state, three-way valve 194 allows fluid, such as water or PD fluid, to flow from fluid inlet 224 through normally open fluid outlet 228. In the normally open state, three-way valve 194 allows fluid, such as water or PD fluid, to flow from fluid inlet 224 through normally closed fluid outlet 228.

Higher fluid pressure through fluid inlet 224 helps to seal membrane or stopper 230 against both normally closed port 226*p* and normally open port 228*p*, wherein the pressure in normally closed fluid outlet 226 and normally open fluid outlet 228 is less. It should be appreciated however that the pressure delta that helps to seal membrane or stopper 230) against beveled ports 226*p*, 228*p*, also fights against (i) the magnetic force induced when coil 164 is energized to open normally closed fluid outlet 226 and (ii) the force of compression spring 208 when coil 164 is de-energized to open normally open fluid outlet 226. Described herein is structure and associated functionality for ensuring that normally closed fluid outlet 226 is properly opened when it is supposed to be.

Solenoid Valve Methodology To Reduce Noise

As previously discussed, there is a desire and need for reliable methodologies for reducing noise caused by solenoid valves in medical fluid delivery operations. Noise reduction is particularly pertinent for peritoneal dialysis systems, which operate close to a patient, and which may occur during the night when patients are sleeping and reduced noise is of the essence. A desirable PD system is one in which the noise level is maintained below 33 decibels. Various embodiments of the present disclosure describe systems and methods for reducing noise in PD systems using solenoid valves. In particular, various embodiments describe systems and methods for controlling the movement of the solenoid valve to minimize the amount of sound (noise) that occurs at impact during activation and deactivation of the valve. The systems and methods in general include the slowing of the movement of the valve plunger within the valve coil. Any modification that slows the movement of the valve will yield a lesser impact with the valve housing and generate a lower level of impact sound. The various embodiments discussed herein include the use of low pass filtering. NPN transistors, MOSFETs, and pulse width modulation, among others.

In at least one embodiment, a method to slow the movement of the valve plunger involves ramping up the voltage applied to the solenoid coil (e.g., during valve activation) and/or ramping down the voltage applied to the solenoid coil (e.g., during valve deactivation). In one aspect, a low pass filter may be applied to an existing application of voltage in order to provide the ramping up and/or ramping down effect. Since the steady state operation of the valve may typically use in one example approximately 0.3 A, the resistor may need to be small, and the size of the capacitor may need to be large. For example, the size of a capacitor to obtain a time constant around 25 ms may be approximately 25 mF if a resistor of 1 Ohms is chosen.

In at least one embodiment, transistors may be used to ramp up and/or ramp down the voltage applied to a solenoid coil of a valve in order to slow down the movement of the plunger and reduce noise. In some aspects, the transistors may provide linear control over the voltages applied to the coils. The different variants of transistors (e.g., NPN-transistor, MOSFET-transistor, etc.) may provide different capabilities and positive aspects for effectively reducing the noise of solenoid valves, which is discussed in relation to FIGS. 4 through 8.

Figure 4:
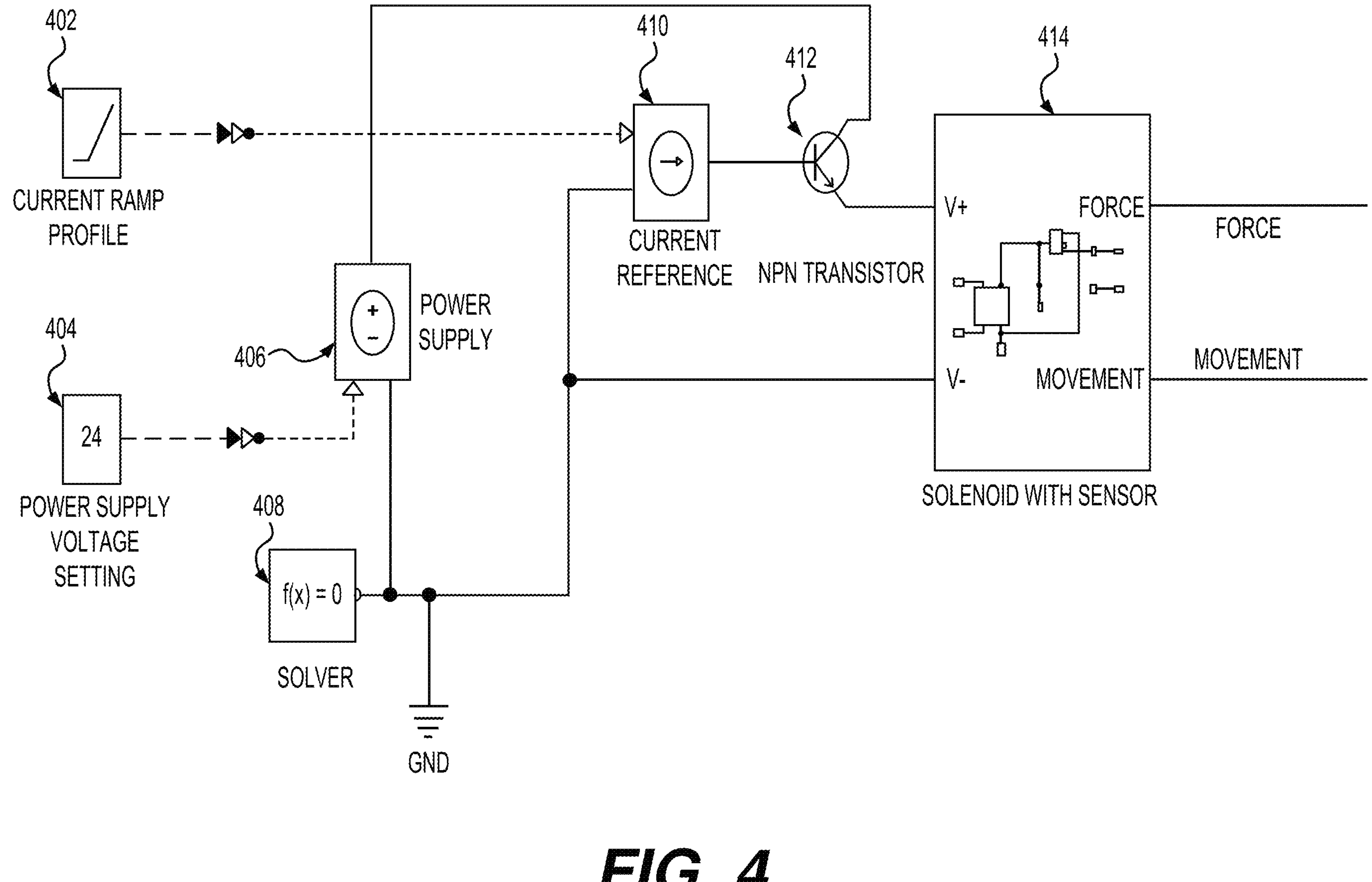
FIG. 4 is a simulation of a circuit of a system for reducing noise created by solenoid valve operation in a medical fluid system using an NPN transistor, according to a non-limiting embodiment of the present disclosure.

FIG. 4 is a simulation of a circuit for a system for reducing noise created by solenoid valve operation in a medical fluid system using an NPN transistor, according to a non-limiting embodiment of the present disclosure. The system may include a valve 414 (e.g., valve 154 or valve 194 discussed above) of a PD system being controlled electrically by an NPN transistor 412. For example, as shown in FIG. 4, a power supply 406 (e.g., of an NPU) may control the NPN-transistor 412 through a control signal (e.g., an ON/OFF signal). The control signal may be generated based on a power supply voltage setting 404. The control signal sent to the NPN-transistor may comprise and/or generate an input current to the NPN-transistor (e.g., as shown in current ramp profile 402). The input current may cause the NPN transistor to transition the valve 414 to apply a voltage to the solenoid coil. If the input current is kept low, (e.g., so that the input current does not exceed the non-saturated zone of the NPN transistor 412), the voltage applied to the solenoid coil may be ramped up by ramping up the current to the NPN transistor 412 (e.g., as shown by current ramp profile 402). The behavior is similar to the low pass filter without the need for supplying significant capacitance or resistance with the solenoid coil. In some embodiments, the system may further include a solver device 408, which is used to determine when to provide requisite signals to the NPN transistor 412 to cause the valve to ramp up or ramp down the voltage applied to the solenoid coil. The simulation of the circuit may cause effects in the physical domain (e.g., through valve 414). For example, the NPN-transistor 412 may cause the valve 414 to apply force upon the plunger and cause movement of the plunger.

Figure 5:
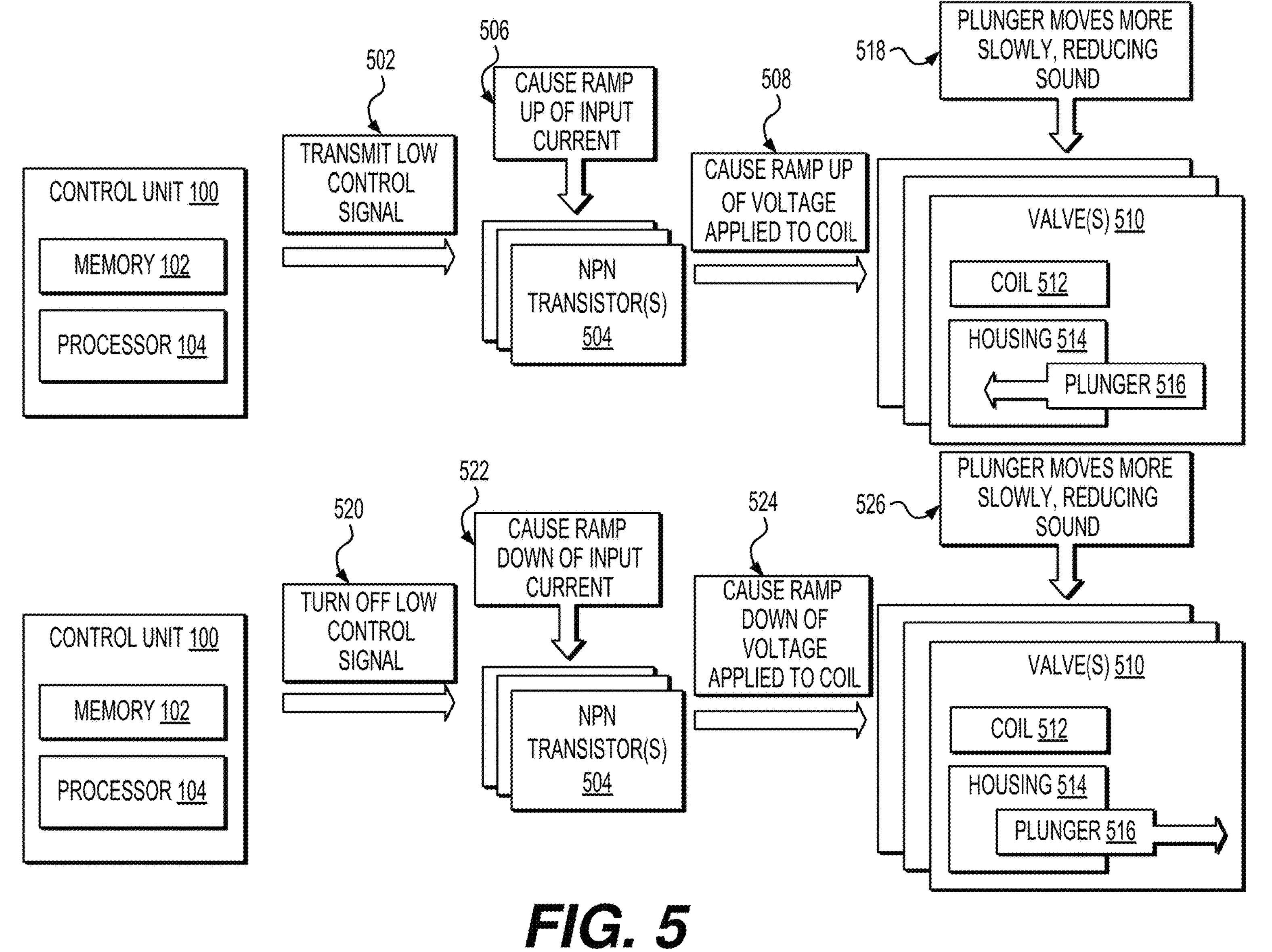
FIG. 5 is a block diagram illustrating a system and method for reducing noise created by solenoid valve operation in a medical fluid system using an NPN transistor, according to a non-limiting embodiment of the present disclosure.

FIG. 5 is a block diagram illustrating a system and method for reducing noise created by solenoid valve operation in a medical fluid system using an NPN transistor, according to a non-limiting embodiment of the present disclosure. The system may comprise control unit 100 of PD system 10, as discussed above, which may further comprise a memory 102 and a processor 104. The system may further comprise a plurality of NPN transistors 504 configured to control a plurality of valves 510 (e.g., valve 154 or valve 194 discussed above) in response to control signals received from control unit 100. As discussed above, the plurality of valves 510 may comprise solenoid valves (e.g., valves 154 or 194) used by a PD system to control fluid fresh and used PD fluid flow. Thus, each valve 510 may comprise a corresponding housing 514, a respective solenoid coil 512, and a corresponding plunger 516. Each valve 510 may be configured to activate a flow of fluid through a tube of the PD system by applying, via the respective NPN transistor 504, voltage to the respective solenoid coil 512 to move the corresponding plunger 516 within the corresponding housing 514. Each valve may also be configured to close the flow of fluid through the tube by un-applying (e.g., decreasing), via the respective NPN transistor 504, the voltage to the corresponding coil 512 to move the corresponding plunger 516 in a direction opposite of the corresponding housing 514 (e.g., to occlude the corresponding tube).

In order to reduce noise associated with valve activation for a given valve (e.g., the opening of a valve), control unit 100 may be configured to (e.g., via the processor 104 processing computer-executable instructions stored in the memory 102) transmit a low control signal to the NPN transistor 504 associated with the valve 510 (block 502). The low control signal may cause a ramping up of input current to the NPN transistor 504 (block 506). The ramping up of the input current to the NPN transistor 504 may result in a ramping up of the voltage applied to a corresponding coil 512 of the valve 510 (block 508). As previously discussed, a ramping up of voltage applied to the solenoid coil 512 (e.g., as opposed to a sudden application of voltage) causes a plunger 516 to move more slowly during activation. The slower movement can thus reduce the sound generated by the corresponding plunger of the valve 510 (block 518).

In order to reduce noise associated with valve deactivation for a given valve (e.g., the closing of a valve), control unit 100 may be configured to turn off the low control signal to the NPN transistor 504 associated with the valve (block 520). The turning off of the control signal may cause a ramping down of the input current supplied to the NPN transistor 504 (block 522). The ramping down of the input current to the NPN transistor 504 may result in a ramping down of the voltage applied to the corresponding coil 512 of the valve 510 (block 524). As previously discussed, a ramping down of voltage applied to the solenoid coil 512 (e.g., as opposed to a sudden termination of voltage) causes the plunger 516 to move more slowly in the opposite direction from the housing 514 during deactivation. The slower movement can thus reduce the sound generated by the corresponding plunger of the valve 510 (block 526).

MOSFET is another transistor that can be used to slow down the movement of the plunger in a solenoid valve and therefore reduce noise. Further, using a MOSFET to control the voltage applied to the solenoid coil may overcome unwanted heat caused by the relatively high resistance in the NPN transistor.

Figure 6:
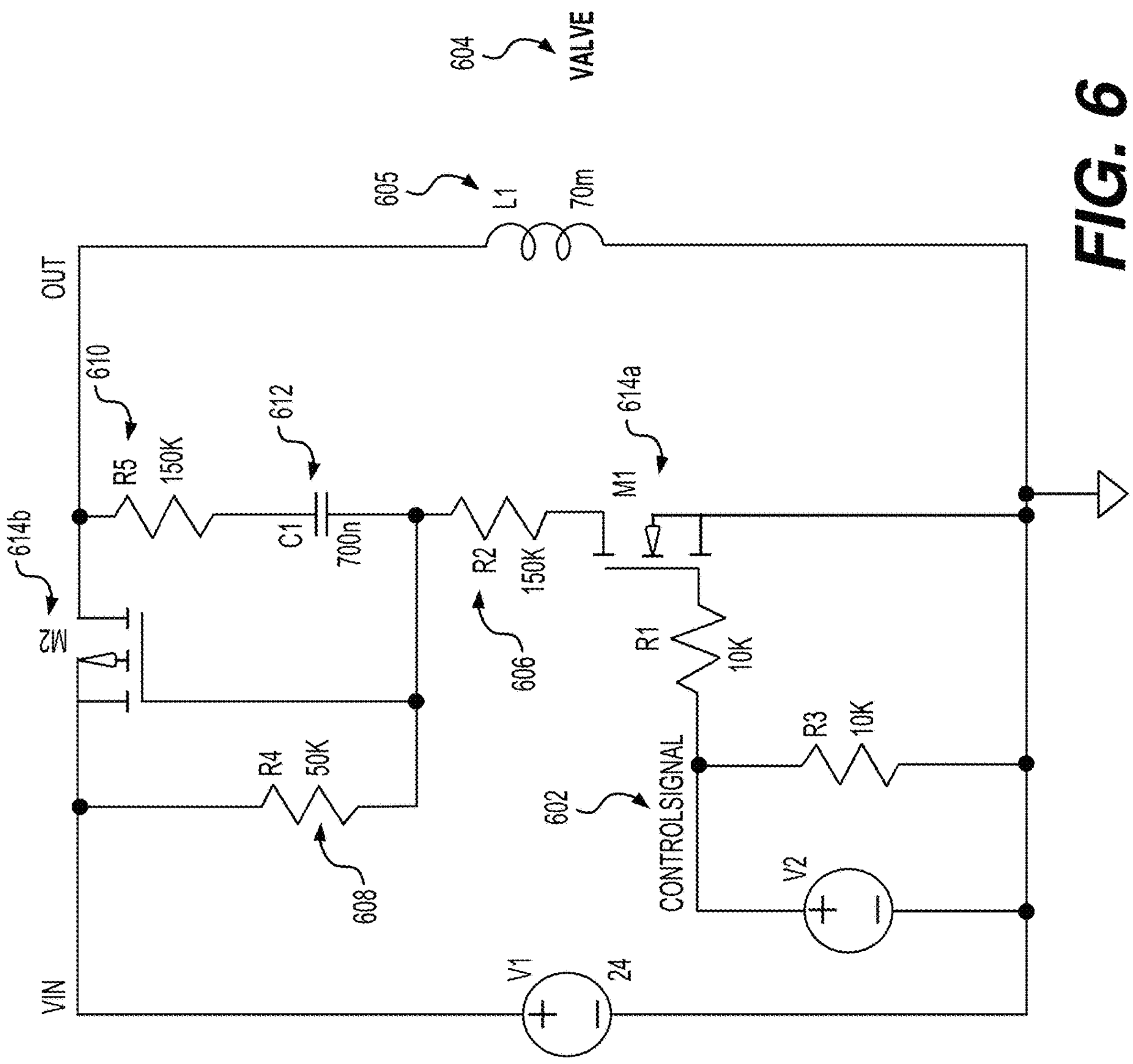
FIG. 6 is a circuit diagram showing a system for reducing noise created by solenoid valve operation in a medical fluid system using a MOSFET, according to a non-limiting embodiment of the present disclosure.

FIG. 6 is a circuit diagram of a system for reducing noise created by solenoid valve operation in a medical fluid system using a MOSFET, according to a non-limiting embodiment of the present disclosure. The circuitry of the system may facilitate the slow application of voltage (e.g., by ramping up) to a solenoid coil 605 of the valve 604, and the slow un-application of the voltage (e.g., by ramping down) to the solenoid coil 605 of the valve 604, using P-Channel MOSFETs 614*a* and 614*b*. The control signal 602 may comprise a simple digital output from a control unit 100 and/or other digital circuitry. When the digital control signal is high (e.g., a "one" and/or a "true"), one or both of the MOSFET 614*a* and 614*b* may cause the ramping up of voltage applied to the solenoid coil 605 until the applied voltage reaches the same voltage as an input voltage, Vin for that valve 604. In some aspects, voltage Vin may refer to the threshold voltage required for a valve to sufficiently activate (e.g., by causing the complete movement of the plunger to an end point within the housing). If the digital control signal generated by the control unit 100 turns low (e.g., a "zero" or "false"), the applied voltage may slowly ramp down towards a voltage of 0V. The time of the up ramping and down ramping can be adjusted by changing the values of one or more resistors and capacitors of the circuit, for example, resistors R2 606, R4 608, and R5 610, and capacitor C1 612. In some aspects, the one or more resistors and/or one or more capacitors may be serially arranged, e.g., as shown in the circuit of FIG. 6. The ramping up and ramping down of the voltage applied to the solenoid coil 605 may add a turn-on and turn-off delay, respectively, to the control of the solenoid coil 605. To shorten this delay an initial ramp offset circuit may be added to the circuit to generate additional voltage of an offset value to be applied to the coil 605. This offset value can be set to a voltage that is near the lowest voltage applied by the one or more MOSFET 614*a*, 614*b* to the solenoid coil 605. In one embodiment, the offset value of the ramp offset voltage can be set by adjusting the feedback resistor R5 610 in relation to resistors R2 606 and R4 608. An example control signal sent to the MOSFET 614*b* and an example voltage applied to the solenoid coil 605 may be seen in FIG. 7A.

Figure 7A:
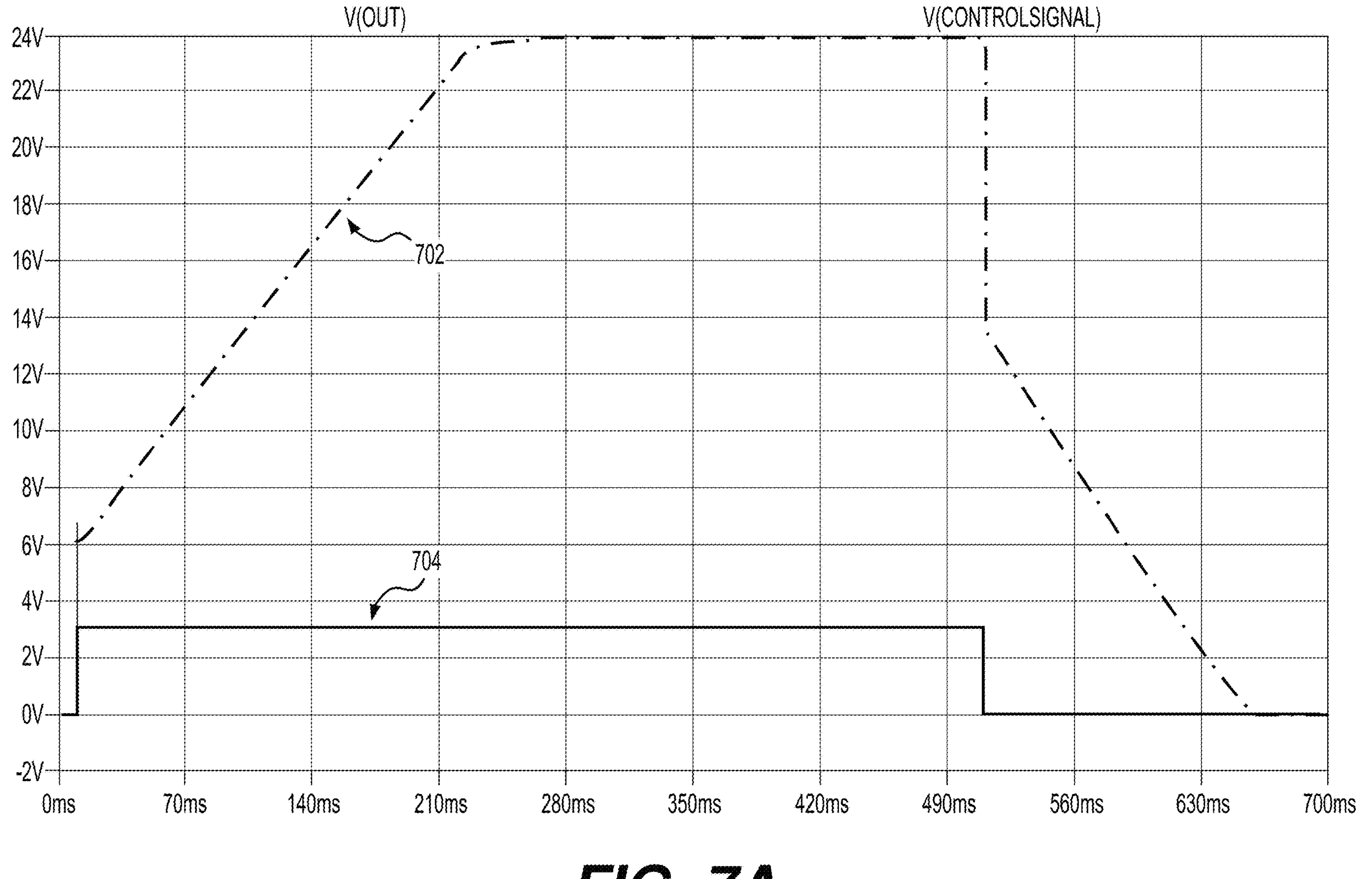
FIG. 7A is a graph illustrating a control signal and an applied voltage for reducing noise created by solenoid valve operation in a medical fluid system using a MOSFET, according to a non-limiting embodiment of the present disclosure.

FIG. 7A is a graph illustrating a control signal 704 and an applied voltage 702 for reducing noise created by solenoid valve operation in of medical fluid system 10 using a MOSFET, according to a non-limiting embodiment of the present disclosure. As previously discussed, the control signal 704 may be a digital signal generated by a control unit 100 and may be transmitted to the MOSFET to cause the MOSFET to generate the applied voltage 704. As shown in FIG. 7A, the high level (i.e., the supply level) of the digital control signal 704 is at 3V, whereas the low level (i.e., the reference level) of the digital control signal is at 0V. The MOSFET allows the applied voltage 702 to ramp up (as shown in the positive slope from approximately Oms to approximately 210 ms) responsive to the high digital control signal 704. However, when the digital control signal 704 is set to the low level (e.g., at 0V), the MOSFET causes the applied voltage 702 to ramp down (as shown by the negative slope from approximately 500 ms to 650 ms). The relatively vertical increases and decreases of the applied voltage 702 (at Oms and 500 ms, respectively) may result from an offset voltage applied to the solenoid coil to overcome delays caused by the ramping up and ramping down, respectively.

Figure 7B:
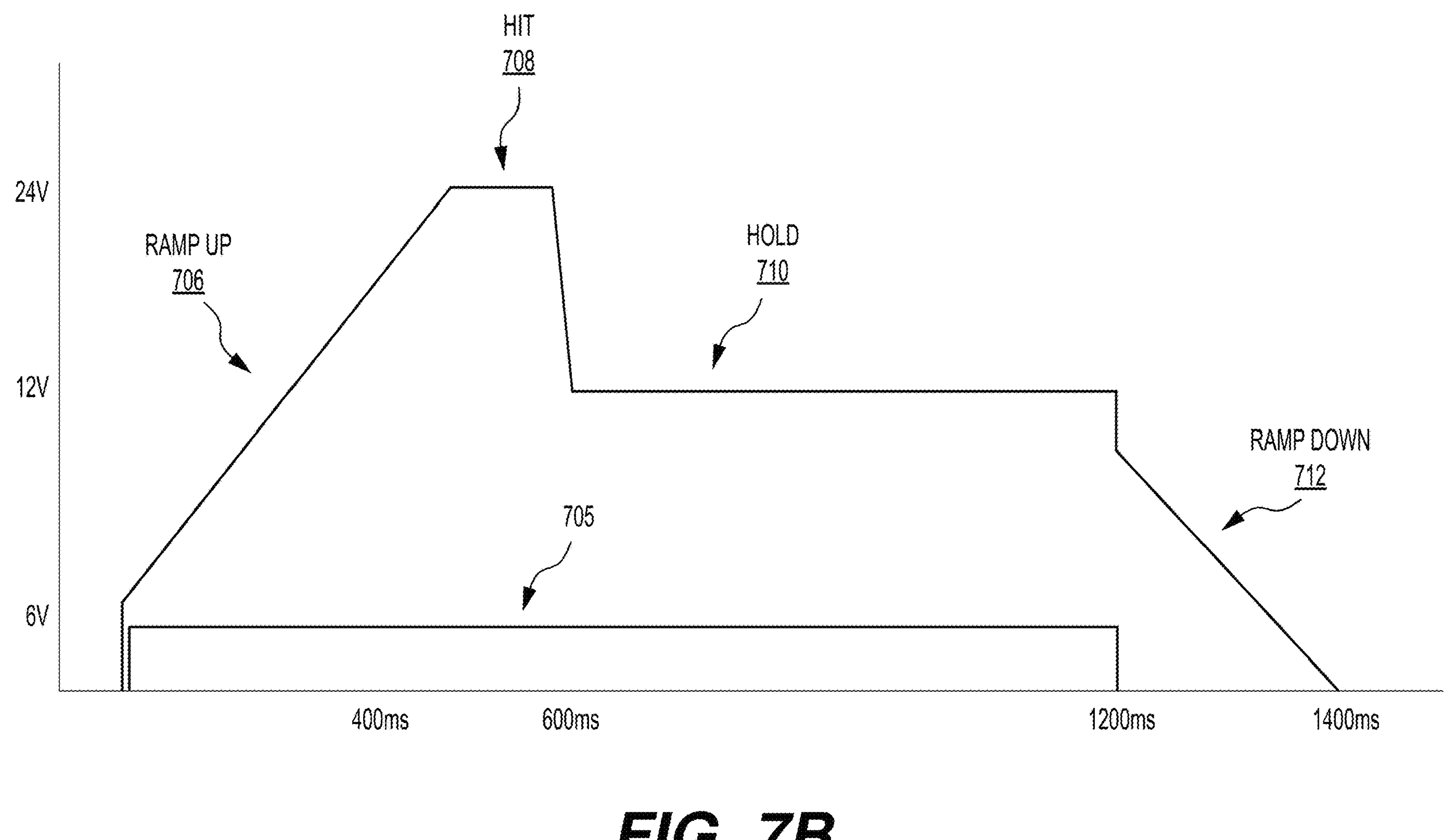
FIG. 7B is a graph illustrating an applied voltage for reducing noise created by solenoid valve operation in a medical fluid system using pulse width modulation ("PWM"), according to a non-limiting embodiment of the present disclosure.

FIG. 7B is a graph illustrating an applied voltage for reducing noise created by solenoid valve operation in a medical fluid system using pulse width modulation ("PWM"), according to a non-limiting embodiment of the present disclosure. The applied voltage may be responsive to a control signal (e.g., control signal 705) generated by a control unit 100 and received by an input/output (I/O) driver associated with the solenoid valve to energize (e.g., activate) the solenoid valve. Responsive to the command, the I/O driver may apply and ramp up 706 a PWM voltage to the solenoid coil associated with the valve. For example, the I/O driver may ramp up the PWM voltage from approximately 6V to 24V in 2 ms to 400 ms. The applied voltage may cause the plunger of the valve to move towards the housing. After the plunger in the valve has reached its end point (e.g., within the housing) (e.g., as may likely occur at or before the stage indicated as "hit" 708), the PWM duty cycle can be lowered, which lowers power consumption and heat generation in the PD system 10. For example, the control unit 100 may command (e.g., via a second control signal) the I/O driver to ramp down the PWM signal applied to the corresponding coil until reaching a predetermined voltage. For example, the I/O driver may maintain a PWM signal at 12V (e.g., as indicated by "hold" 710 in FIG. 7B from 600 ms to 1200 ms). When the valve is to be deactivated (e.g., closed and/or shut off), the I/O driver may ramp down 712 the PWM to 0 V (e.g., as shown in FIG. 7B between 1200 ms to 1400 ms). In some embodiments, if the I/O driver ramps up the PWM voltage slowly as indicated, the plunger in the valve may reach its end point within the housing during the ramp up phase 706. Since the plunger may hit the end point as a result of lower power being applied to the solenoid valve, the sound level associated with hitting the endpoint may be lower. Furthermore, a full power level at the stage indicated as "hit" 708 can ensure that the plunger hits the seal even if the load has increased. After this stage, the power consumption can be lowered in (e.g., as in "hold" phase 710).

Figure 8:
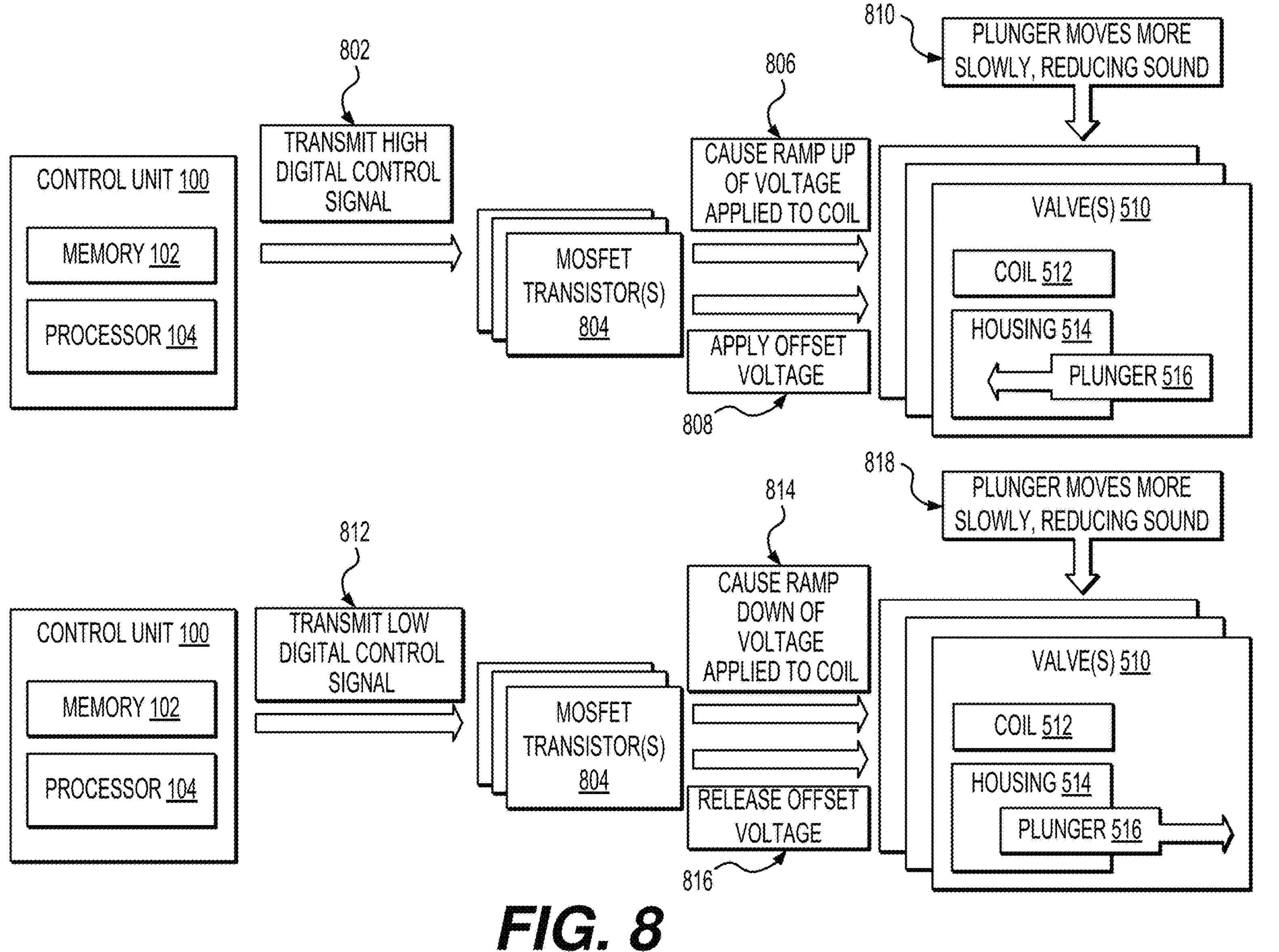
FIG. 8 is a block diagram illustrating a system and method for reducing noise created by solenoid valve operation in a medical fluid system using a MOSFET, according to a non-limiting embodiment of the present disclosure.

FIG. 8 is a block diagram illustrating a system and method for reducing noise created by solenoid valve operation in a medical fluid system using a MOSFET, according to a non-limiting embodiment of the present disclosure. The system may comprise control unit 100 of PD system 10, as discussed above, which may further include a memory 102 and a processor 104. The system may further comprise a plurality of MOSFETs 804 configured to control a plurality of valves 510 in response to digital control signals received from the control unit 100. As discussed above, the plurality of valves 510 may comprise solenoid valves 154, 194 (FIGS. 2 and 3) used by PD system 10 to control fresh and used PD fluid flow. Thus, each valve 510 may comprise a corresponding housing 514, a respective solenoid coil 512, and a corresponding plunger 516. Each valve 510 may be configured to activate a flow of fluid through a tube of PD system 10 by applying, via the respective MOSFET 804, voltage to the respective solenoid coil 512 to move the corresponding plunger 516 within the corresponding housing 514. Each valve may also be configured to close the flow of fluid through the tube by un-applying (e.g., decreasing), via the respective MOSFET 804, the voltage to the corresponding coil 512 to move the corresponding plunger 516 in a direction opposite of the corresponding housing 514 (e.g., to occlude the corresponding tube).

In order to reduce noise associated with valve activation for a given valve (e.g., the opening of a valve), the control unit 100 may be configured to (e.g., via the processor 104 processing computer-executable instructions stored in the memory 102) transmit a high digital control signal (e.g., a digital signal corresponding to the "high" level, the supply voltage, and/or the binary output of "1") to the MOSFET 804 associated with the valve 510 (block 802). As is to be appreciated, a MOSFET, unlike a NPN transistor, requires less power for the gate to operate (e.g., to activate the MOSFET), and thus may not require a ramp up of an input current as was the case for the NPN transistor. The high control signal may cause the MOSFET 804 to apply and a ramp up voltage to a corresponding coil 512 of the valve 510 (block 806). As previously discussed, a ramping up of voltage applied to the solenoid coil 512 (e.g., as opposed to a sudden application of voltage) causes a plunger 516 to move more slowly during activation. The slower movement can thus reduce the sound generated by the corresponding plunger of the valve 510 (block 810). In some embodiments, the slow ramp up of the voltage applied to the coil may cause an unwanted delay in the activation of the valve. Thus an offset voltage may also be applied to the solenoid coil 512 (block 808) via a ramp offset circuit.

In order to reduce noise associated with valve deactivation for a given valve (e.g., the closing of a valve), the control unit 100 may be configured to transmit a low digital control signal (e.g., a digital signal corresponding to the "low" level, the reference or ground voltage, and/or the binary output of "0") to the MOSFET 804 associated with the valve (block 812). The low control signal may cause the MOSFET 804 to apply a ramp down voltage to the corresponding coil 512 of the valve 510 (block 814). As previously discussed, a ramping down of the voltage applied to the solenoid coil 512 (e.g., as opposed to a sudden removal of voltage) causes the plunger 516 to move more slowly during deactivation. The slower movement can thus reduce the sound generated by the corresponding plunger of the valve 510 (block 818). In some embodiments, the slow ramp down of the voltage applied to the coil may cause an unwanted delay in the deactivation of the valve. Thus an offset voltage may also be released from the solenoid coil 512 (block 816) via the ramp offset circuit.

In at least one embodiment, pulse width modulation ("PWM") may be used to ramp up and/or ramp down the voltage applied to a solenoid coil of a valve in order to slow down the movement of the plunger and reduce noise. Additionally, techniques employing PWM may overcome issues caused by relying on transistors to gradually decrease (e.g., ramp down) voltage applied to the solenoid coil during deactivation. For example, lowering the applied voltage may induce a lower magnetic field in the solenoid coil, resulting in a lower force acting on the plunger. Since a valve may be working against a low or high pressure, the valve may need a full force to change from closed to open during activation, or from open to closed during deactivation. A system and method that relies on PWM signals for valve activation and deactivation may overcome these issues. Further, controlling the activation and/or deactivation of a valve through methods relying on pulse width modulation, as discussed herein, may also involve ramp ups and/or ramp downs in the voltage applied to the solenoid coil, but only during a transition period. After the transition period (e.g. during the start of an activation or the start of the deactivation of a valve), the pulse width modulation technique may involve eventually applying the full input voltage Vin for a sustained duration to guarantee that the plunger properly moves to the intended end point (e.g., inside the housing during activation, and towards a position that occludes the valve during deactivation).

The application of PWM for valve activation may involve a pulsed application of voltage (rapidly switching ON/OFF) to the solenoid coil, while ramping up the application until the plunger has moved. The application of PWM for valve deactivation may involve a diminishing pulsed application of voltage to the solenoid coil, while ramping down the application until the plunger has moved. This may allow for a slower movement of the plunger, a lower impact at valve activation/deactivation, and thus a reduction in noise. Another benefit with this approach is that the PWM is available during normal operation as well. Thus, using PWM for valve activation and/or deactivation may lower the overall power demand and keep the PD system 10 cooler during operation.

In at least one embodiment, an example power-on/power-off cycle for a solenoid valve utilizing PWM involves the control unit 100 transmitting a command (e.g., via a control signal) to an input/output (I/O) driver associated with a valve to energize (e.g., activate) the valve. Responsive to the command, the I/O driver may apply and ramp up a PWM voltage to the solenoid coil associated with the valve. For example, the I/O driver may ramp up the PWM voltage from 0% to 100% in 2 ms to 75 ms (e.g., 2 ms to 10 ms). The applied voltage may cause the plunger of the valve to move towards the housing. After the plunger in the valve has reached its end point (e.g., within the housing), the PWM duty cycle can be lowered, which may lower power consumption and as well as heat generation in the PD system 10. For example, the control unit 100 may command (e.g., via a second control signal) the I/O driver to ramp down the PWM signal applied to the corresponding coil to a duty cycle that is 25% or above (e.g., 50% or above). When the valve is to be deactivated (e.g., closed and/or shut off), the I/O driver may ramp down the PWM to 0% (e.g., from 50%) in 25 to 75 ms (e.g., approximately 50 ms).

Figure 9:
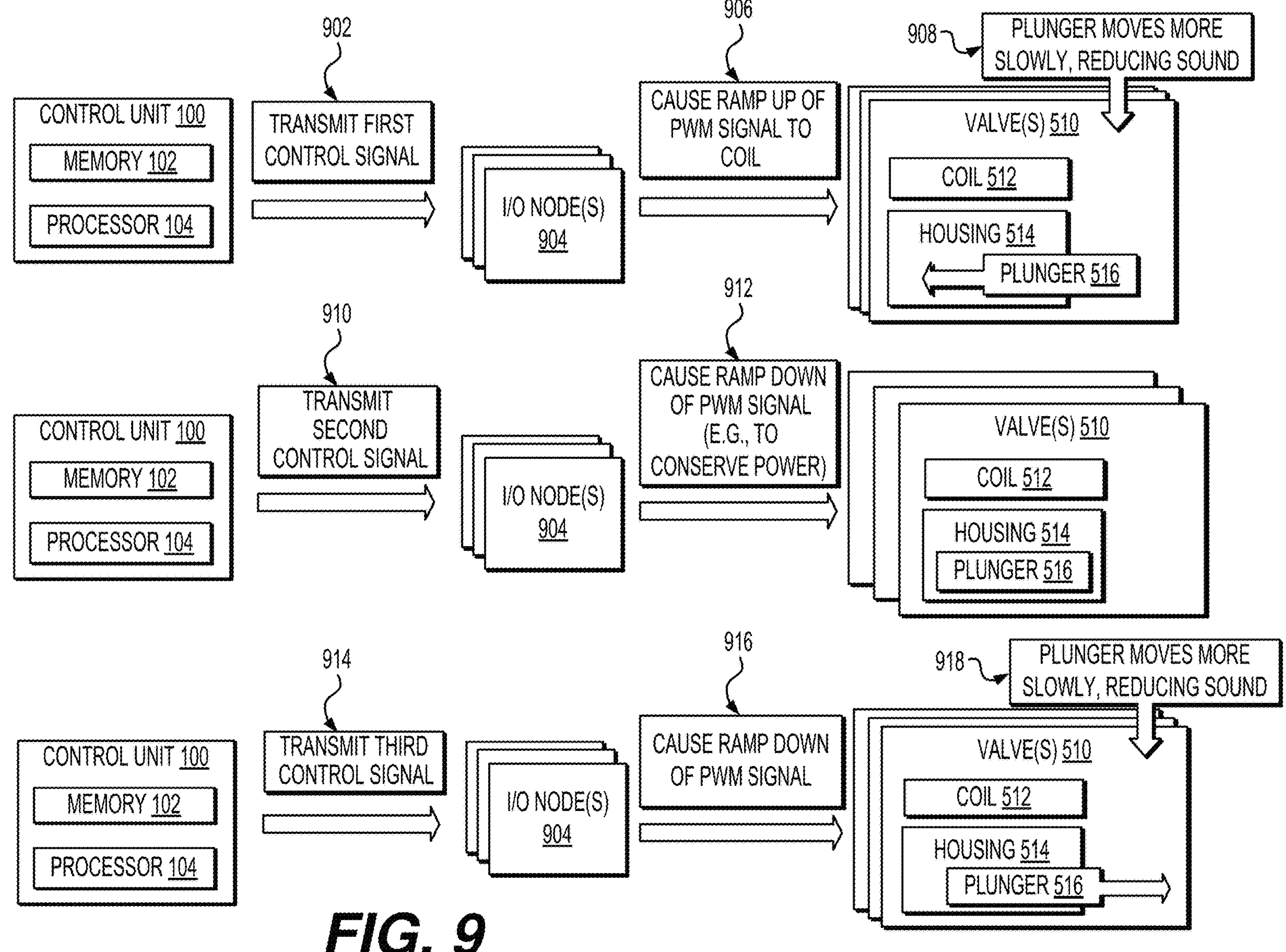
FIG. 9 is a block diagram illustrating a system and method for reducing noise created by solenoid valve operation in a medical fluid system using pulse width modulation ("PWM"), according to a non-limiting embodiment of the present disclosure.

FIG. 9 is a block diagram illustrating a system and method for reducing noise created by solenoid valve operation in a medical fluid system using pulse width modulation ("PWM"), according to a non-limiting embodiment of the present disclosure.

The system may comprise the control unit 100 of PD system 10, as discussed above, which may further comprise a memory 102 and a processor 104. The system may further comprise a plurality of input/output ("I/O") nodes 904 (also referred to as I/O drivers) configured to control a plurality of valves 510 in response to control signals received from the control unit 100. As discussed above, the plurality of valves 510 may comprise solenoid valves 154, 194 (FIGS. 2 and 3) used by PD system 10 to control fresh and used PD fluid flow: Thus, each valve 510 may comprise a corresponding housing 514, a respective solenoid coil 512, and a corresponding plunger 516. Each valve 510 may be configured to activate a flow of fluid through a tube of PD system 10 by applying, via a respective I/O node 904, voltage to the respective solenoid coil 512 to move the corresponding plunger 516 within the corresponding housing 514. Each valve may also be configured to close the flow of fluid through the tube by un-applying (e.g., decreasing), via the respective I/O node 904, the voltage to the corresponding coil 512 to move the corresponding plunger 516 in a direction opposite of the corresponding housing 514 (e.g., to occlude the corresponding tube).

In order to reduce noise associated with valve activation for a given valve (e.g., the opening of a valve), the control unit 100 may be configured to (e.g., via the processor 104 processing computer-executable instructions stored in the memory 102) transmit a control signal to the I/O node associated with the valve (block 902). The control signal may be digital or an analog signal. The control signal, referred to as first control signal to distinguish from subsequent control signals discussed herein, may command the I/O node 904 to apply and ramp up a PWM signal (e.g., voltage) to the solenoid coil 512 of the valve 510 (block 906). For example, the I/O node can ramp up a duty cycle of the pulsed application of voltage to the corresponding coil from 0% to 100% in approximately 50 ms. The ramping up of voltage applied to the solenoid coil 512 (e.g., as opposed to a sudden application of voltage) causes the plunger 516 of the valve 510 to move more slowly during activation. The slower movement can thus reduce the sound generated by the corresponding plunger of the valve 510 (block 908). After the plunger 516 reaches an end position (e.g., within housing 514) during the valve activation, the control unit 100 may transmit a second control signal to the I/O node 904 (block 910). The second control signal may cause the I/O node to ramp down the PWM signal to the corresponding coil (block 912). For example, the duty cycle may be ramped down (e.g., from 100%) to a duty cycle that is at least 25%, for example, at approximately 50%, of the Vin. The ramp down at block 912 may help to conserve power of the PD system 10.

In order to reduce noise associated with valve deactivation for a given valve (e.g., the closing of a valve), the control unit 100 may be configured to transmit a third control signal to the I/O node 904 associated with the valve (block 914). The third control signal, which may comprise a digital or an analog signal, may cause the I/O node 904 to cause a ramp down of the PWM signal (e.g., voltage) applied to the corresponding coil 512 of the valve 510 (block 814). For example, the ramp down of the PWM cycle may reduce the duty cycle to 0%. In some embodiments, ramp down to 0% may occur in between 25 to 75 ms (e.g., in approximately 50 ms). The ramping down of the voltage applied to the solenoid coil 512 (e.g., as opposed to a sudden removal of voltage) causes the plunger 516 to move more slowly during deactivation. The slower movement can thus reduce the sound generated by the corresponding plunger of the valve 510 (block 918). In some embodiments, one or more capacitors may be serially arranged between the control unit 100 and the I/O node 904. The duration of the ramping up and/or the ramping down of the PWM signal may be based on capacitance values of the respective one or more capacitors. Also or alternatively, one or more resistors may be serially arranged between the control unit 100 and the I/O node 904. The duration of the ramping up and/or the ramping down of the PWM signal may be based on the resistance values of the respective one or more resistors.

Assessing the Functionality of Solenoid Valve Activation

As previously discussed, there is a desire and need for reliable methodologies for verifying whether a solenoid valve, e.g., valves 154, 194 (FIGS. 2 and 3), used in PD systems and cyclers (and other medical fluid systems and machines) is activating functionally (e.g., opens correctly when energized). In the absence of such verification systems and methods, hazardous situations may arise. For example, PD system 10 may malfunction, causing treatment to stop, if the machine operates in one mode (e.g., to have valves 154, 194 open and fluid flowing) while the valves are configured in another mode (e.g., valves 154, 194 are actually closed and no fluid is flowing). As discussed herein, the functionality of solenoid valve 154, 194 (e.g., whether the valve is activating correctly) may be determined by analyzing the current drawn by the solenoid operating the valve at the time of activation. A trained classification model may be applied to the current profile to distinguish between valves 154, 194 with solenoids energizing correctly, thus causing a successful activation, versus valves 154,194 having a failed activation.

In some embodiments, the same methodology discussed for assuring a valve 154, 194 is activating or opening properly may be used to verify whether the solenoid valve is deactivating functionally (e.g., closes correctly when de-energized). For example, a current profile of the solenoid operating the valve at the time valve 154, 194 is ordered to deactivate may be received. A classification model may be trained to identify current profiles associated with successful valve deactivations from current profiles associated with unsuccessful valve deactivations. The trained classification model may be applied to the current profile of the solenoid ordered to deactivate to determine whether solenoid valve 154, 194 has functionally deactivated or closed.

Figure 10A:
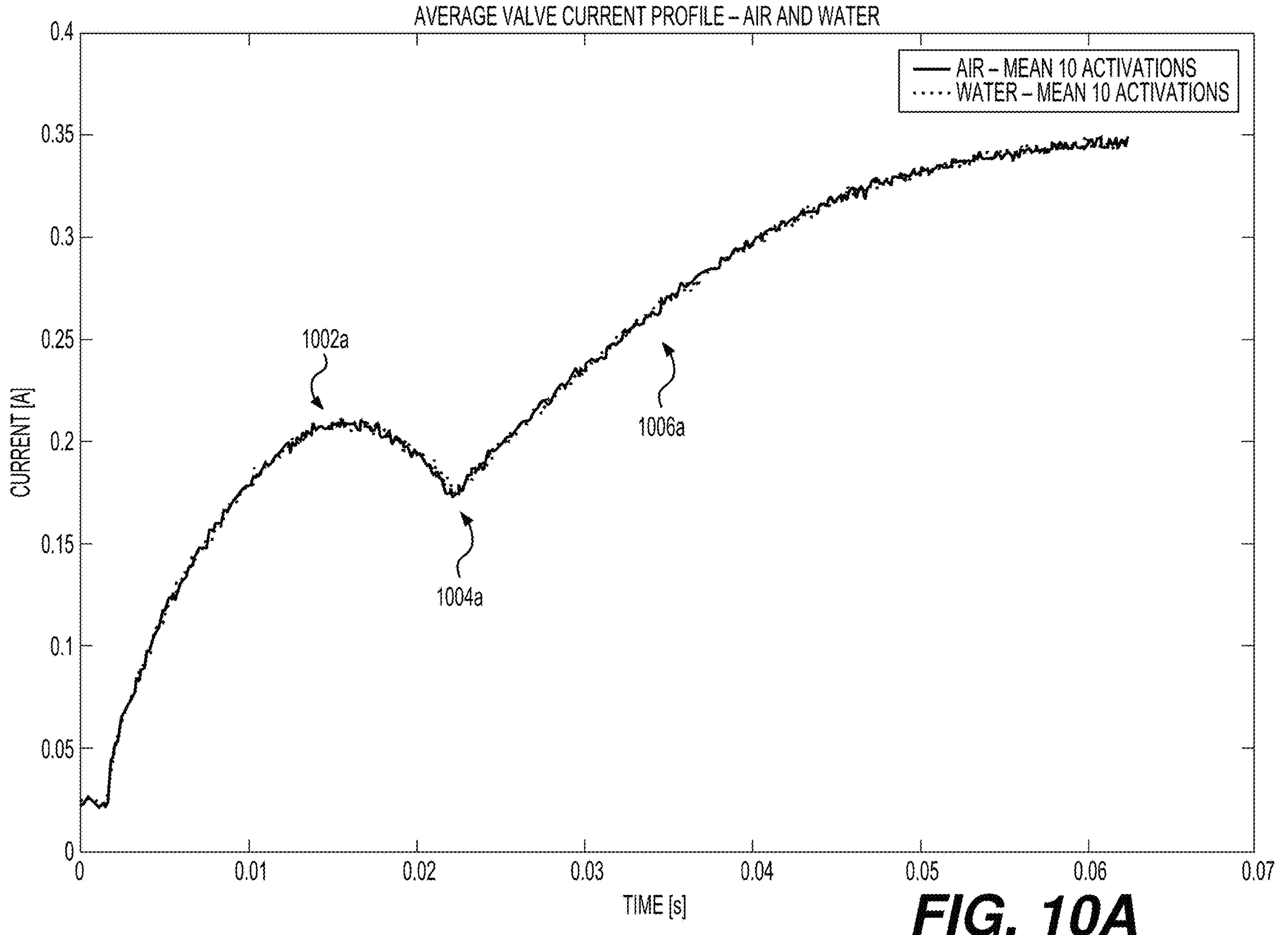
FIG. 10A is a current profile of a solenoid valve having a successful activation, according to an exemplary embodiment of the present disclosure.

FIG. 10A is a current profile of a solenoid valve, e.g., valves 154, 194 (FIGS. 2 and 3), having a successful activation, according to an exemplary embodiment of the present disclosure. Moreover, the graph of FIG. 10A plots the current over time for solenoid coil 164, 204 in the solenoid valve as the solenoid coil is energized during the activation of solenoid valve 154, 194 (e.g., for the opening of the solenoid valve). The graph indicates current measurements taken at frequent intervals (e.g., frequencies of approximately 5 kHz). As shown in FIG. 10A, a successful activation of a solenoid valve 154, 194 causes the current to initially peak (e.g., at location 1002*a*) before beginning to fall. The initial peak and subsequent fall are due to plunger 166, 206 of solenoid valve 154, 194 entering the magnetic field of solenoid coil 164, 204, as the plunger moves in the direction towards the housing of the solenoid valve. The movement of plunger 166, 206 through the magnetic field of solenoid coil 164, 204 generates an opposite voltage that "breaks" the rise of the current through the solenoid coil, resulting in the fall of the current after the initial peak 1002*a*. The plunger 166, 206 hits the end point of its movement (e.g., by resting at the housing of the solenoid valve) at approximately 22 ms, as shown in location 1004*a* of FIG.

10A. The halt in the movement of plunger 166, 206 causes the earlier generation of the opposite voltage to stop, causing the current to rise again, as shown by the rise 1006*a* in FIG. 10A. Therefore, in order to verify that plunger 166, 206 has moved, and therefore solenoid valve 154, 194 has indeed opened when activated, the current profile needs to indicate the "dip" 1004*a*, e.g., at approximately 22 milliseconds. If plunger 166, 206 does not move, the current profile may resemble a regular "RC-curve", i.e., in which no dip occurs.

Figure 10B:
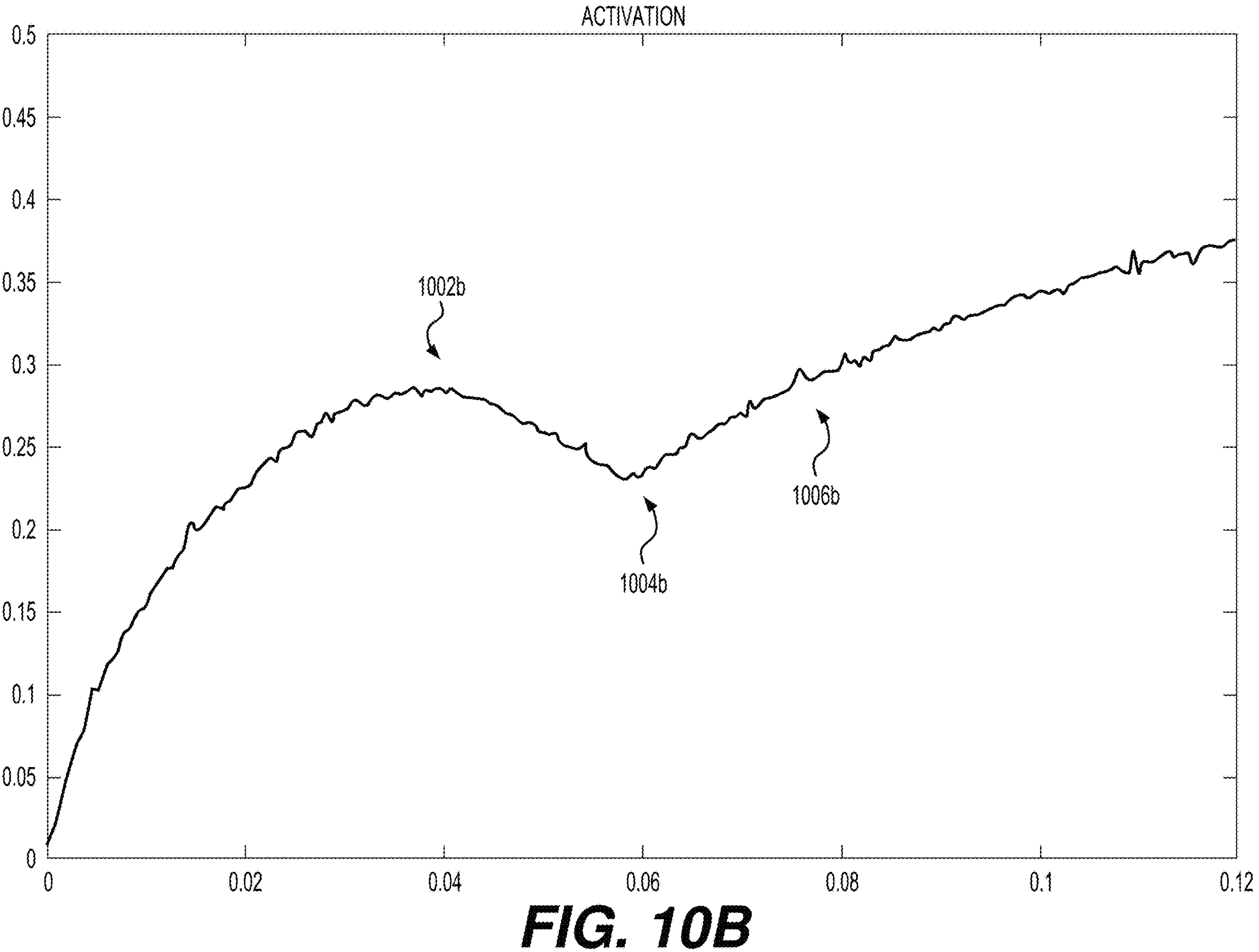
FIG. 10B is another current profile of a solenoid valve having a successful activation, according to an exemplary embodiment of the present disclosure.

FIG. 10B is a second, different current profile of a solenoid valve, e.g., valves 154, 194 (FIGS. 2 and 3), having a successful activation, according to an exemplary embodiment of the present disclosure. Like FIG. 10A, the graph of FIG. 10B plots the current over time for solenoid coil 164, 204 in solenoid valve 154, 194 as the solenoid coil is energized during the activation of the solenoid valve (e.g., for the opening of the solenoid valve). As previously discussed, a successful activation of a solenoid valve 154, 194 causes the current to initially peak (e.g., at location 1002*b*) before beginning to fall. The initial peak and subsequent fall are due to plunger 166, 206 of solenoid valve 154, 194 entering the magnetic field of solenoid coil 164, 204, as the plunger moves in the direction towards the housing of the solenoid valve. The movement of plunger 166, 206 through the magnetic field of solenoid coil 164, 204 generates an opposite voltage that "breaks" the rise of the current through the solenoid coil, resulting in the fall of the current after the initial peak 1002*b*. Here, plunger 166, 206 hits the end point of its movement (e.g., by resting at the housing of solenoid valve 154, 194) at approximately 60 ms, as shown in location 1004*b* of FIG. 10B. The halt in the movement of plunger 166, 206 causes the earlier generation of the opposite voltage to stop, causing the current to rise again, as shown by the rise 1006*b* in FIG. 10B. The differences in current profiles between the graphs of FIGS. 10A and 10B may be based on the type of sensor used, and/or on one or more parameters, configurations, and/or characteristics of the sensors used.

Figure 10C:
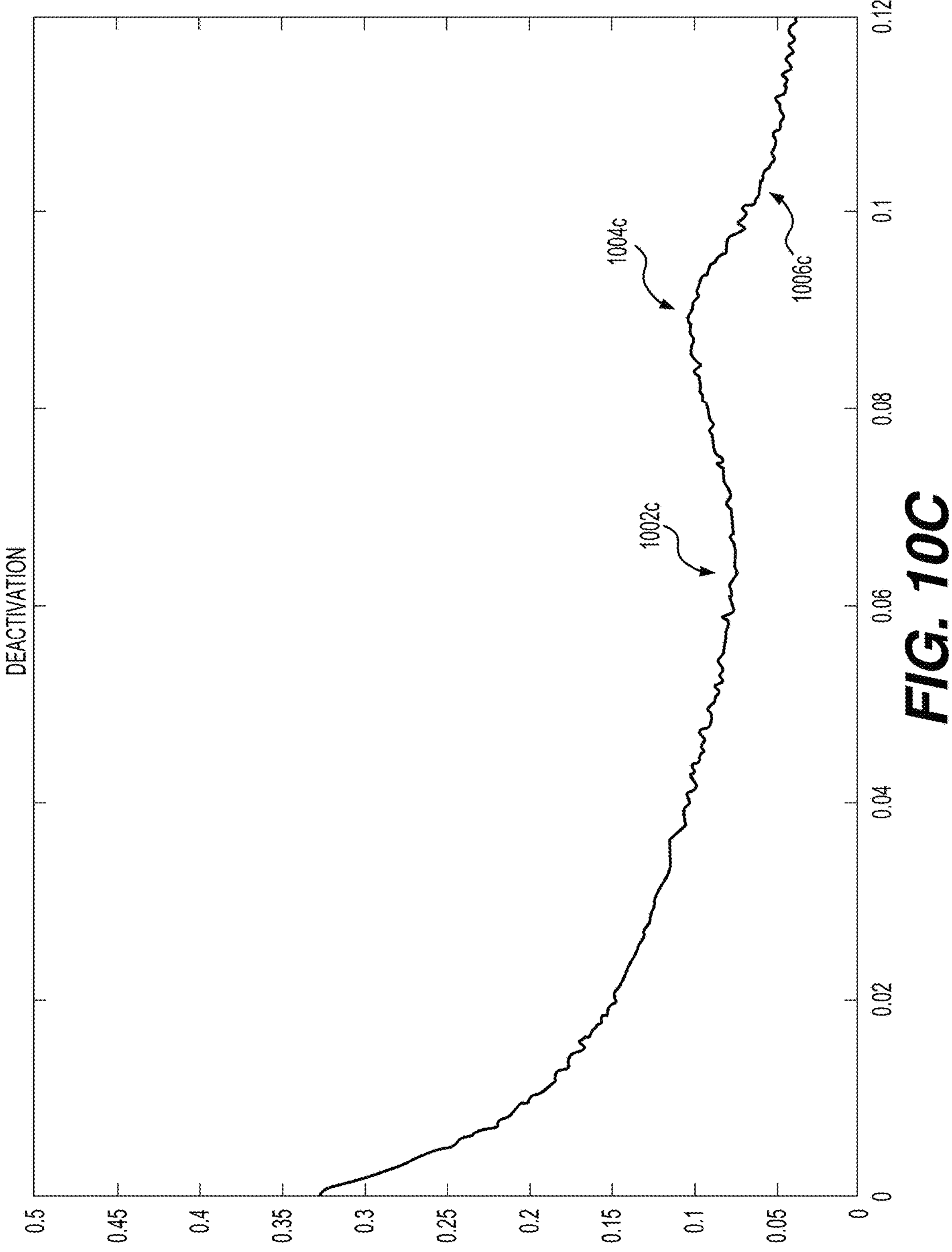
FIG. 10C is a current profile of a solenoid valve having a successful deactivation, according to an exemplary embodiment of the present disclosure.

FIG. 10C is a current profile of a solenoid valve, e.g., valves 154, 194 (FIGS. 2 and 3), having a successful deactivation, according to an exemplary embodiment of the present disclosure. The graph of FIG. 10C plots the current over time for solenoid coil 164, 204 in solenoid valve 154, 194 as the solenoid coil is de-energized during the deactivation of the solenoid valve (e.g., for the closing of the solenoid valve). As shown in FIG. 10C, a successful deactivation of solenoid valve 154, 194 causes the current to initially reach a local minimum (e.g., at location 1002*c*) before beginning to rise. The local minimum and subsequent rise are due to plunger 166, 206 of solenoid valve 154, 194 leaving the magnetic field of solenoid coil 164, 204, as the plunger moves in the direction away from the housing of the solenoid valve. The movement of plunger 166, 206 away from the magnetic field of solenoid coil 164, 204 reduces the voltage causing the fall of the current through the solenoid coil, resulting in the local minimum 1002*c*, before the current rises again. The plunger 166, 206 hits the end point of its movement after it leaves the housing and causes the tube to close at approximately 90 ms, as shown in location 1004*c* of FIG. 10C. The halt in the movement of plunger 166, 206 causes the current to fall again, as shown by the fall 1006*c* in FIG. 10C. Therefore, in order to verify that solenoid valve 154, 194 has indeed closed when deactivated, the current profile needs to indicate the "peak" 1004*c*, e.g., at approximately 90 milliseconds.

Figure 11:
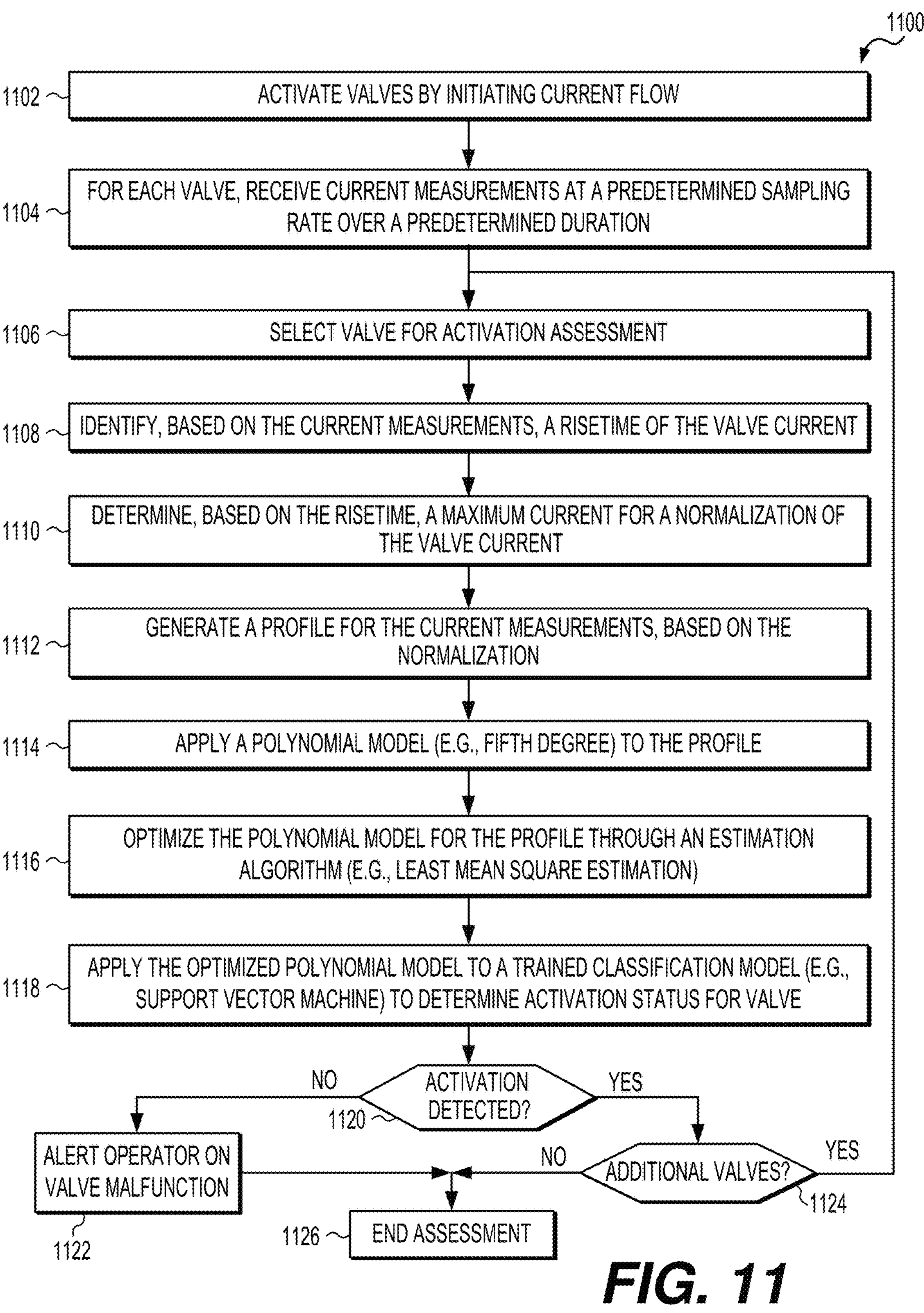
FIG. 11 is a flowchart of an example process for assessing the functionality of a solenoid valve activation, according to an exemplary embodiment of the present disclosure.

FIG. 11 is a flowchart of an example process 1100 for assessing the functionality of a solenoid valve activation, according to an exemplary embodiment of the present disclosure. Process 1100 may be performed by a computing system having one or more processors. Moreover, the processors and/or the computing system may perform process 1100 based on computer-executable instructions stored in the memory of the computing system. As will used and discussed for ease of explanation, the computing system may comprise the control unit 100 of PD system 10, which includes one or more processor 102 and one or more memory 104.

Process 1100 may begin with PD system 10 activating one or more valve 154, 194 (FIGS. 2 and 3) to initiate current flow (block 1102). For example, in the normal course of operation of PD system 10, one or more valve 154, 194 may be commanded to be activated to allow the flow of fluid through tubes associated with the valves. Also or alternatively, during a time when PD system 10 is not servicing a patient (e.g., during pretreatment or preconditioning period of PD system 10), the control unit 100 may cause (e.g., by sending electronic signal commands) valves 154, 194 of the PD system 10 to activate. However, as will be discussed, causing or commanding a valve 154, 194 to activate may not necessarily actuate the valve to open, for example, if the valve is malfunctioning. As discussed herein, process 1100 discloses one or more embodiments of determining whether valve 154, 194 is functioning correctly using the current profile.

Thus, for each valve, the control unit 100 may receive current measurements are a predetermined sampling rate over a predetermined duration (block 1104). It is to be appreciated that the sampling rate would need to be high enough to capture the behavior of valve 154, 194. For example, as shown in the current profile 1200 of FIG. 12 to be discussed herein, the sampling frequency may be approximately 100 to 200 Hz. Further, it is to be appreciated that the duration may need to be long enough to capture the critical period where, for a successfully opening valve 154, 194, the current profile of the valve would indicate a dip (e.g., at approximately 22 milliseconds), as previously discussed in relation to FIGS. 10A and 10B. Blocks 1106 through 1122 may be performed iteratively for each valve being assessed for functionality (e.g., to determine whether valve 154, 194 actually activates). Also or alternatively, blocks 1106 through 1122 may be performed concurrently for each valve.

For example, valve 154, 194 may be selected for activation assessment (block 1106). Based on the current measurements of the valve (received in block 1104), the control unit 100 may identify a risetime of the valve current (block 1108). The risetime may correspond to the generally positive slope of the current measurements over time. For successful valve activations, the risetime may correspond to the positive slop of the current profile after the dip (e.g., after a plunger has ended its movement through the solenoid coil and is within the housing of the solenoid valve). However, as to whether valve 154, 194 has successfully activated may not yet be known, and the dip in the current profile may not be as discernible, a general slope may be assessed to identify the risetime of the current based on the overall current measurements from the time the valve is commanded to be activated until the time when the rise in the current subsides. In some aspects, the risetime may be measured by a duration of time in which the slope of the curve is at least above a predetermined value, such that the end of a risetime may correspond to when the increase in current measurements subsides. For example, based on a sampling frequency shown in FIG. 12 (e.g., of approximately 100 to 200 Hz), an identified risetime may include 20 current measurement values.

At block 1110, the control unit 100 may determine, based on the risetime, a maximum current value for a normalization of the valve current profile. In some embodiments, determining the maximum current value may require comparing the current measurements received for the valve 154, 194 selected at 1106 with the current measurements received for other valves 154, 194 of PD machine 20. It is to be appreciated that the PD system 10 may be configured to conserve power, as may be appropriate, during valve activation. For example, valves 154, 194 of the PD system 10 may be configured to not run at full current. Therefore, the current measurements of valves received may each indicate a different maximum current based on the current that each valve 154, 194 may be allotted to use for activation. Since the maximum current value for each valve may differ, the control unit may determine a maximum current applicable to all or most valves 154, 194. The determined maximum current value may be used to normalize the current measurements received (at block 1102), for example, by dividing each current measurement value by the maximum current value.

At block 1112, a profile for the current measurements may be generated based on the normalization (e.g., using the computed maximum current value). In some aspects, the profile generated may be based on a sample of time that corresponds with the risetime identified in block 1108, e.g., by truncating away any non-relevant time samples.

At block 1114, control unit 100 may apply a polynomial model to the profile. In some embodiments, applying a polynomial model may involve initializing parameters for the polynomial model, for example, by creating initial estimations for and/or randomized values for missing variables and coefficients for the optimization process.

Although increasing the sampling rate and/or frequency may facilitate a more effective polynomial model to fit the current profile, it is contemplated that, in some embodiments, fitting a polynomial model or estimation can be performed without the need to provide increase the sampling extra sampling. Since the behavior of a current over time for valve 154, 194 can be predicted based on the determination of a maximum current (e.g., from block 1110), one or more data points forward in time could be added to the current profile for the valve. This addition may force an estimated polynomial model fit to capture the dynamic behavior of the current profile of the valve better.

Figure 12:
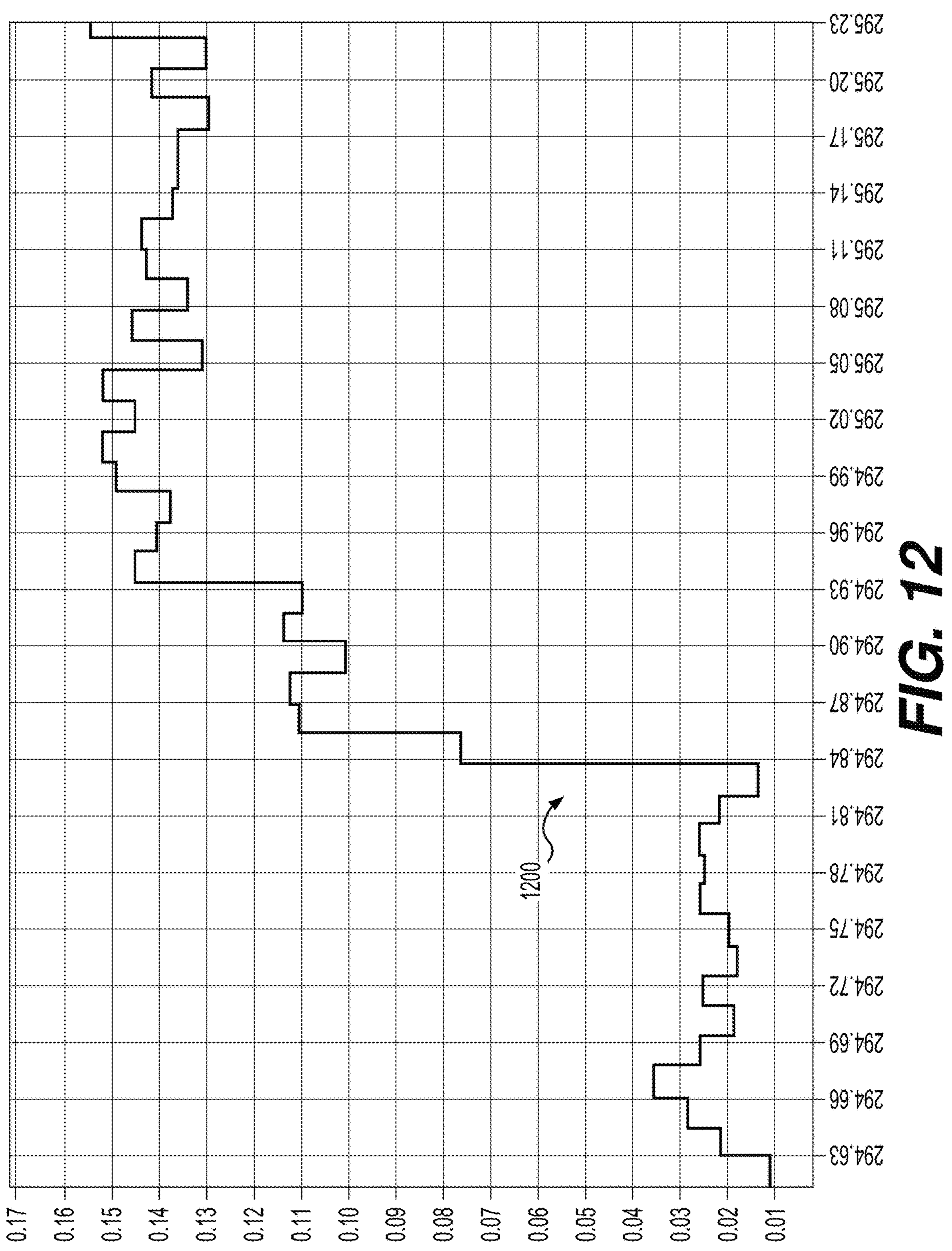
FIG. 12 is a sampled and normalized current profile of a solenoid valve having a successful activation, according to an exemplary embodiment of the present disclosure.
Figure 13:
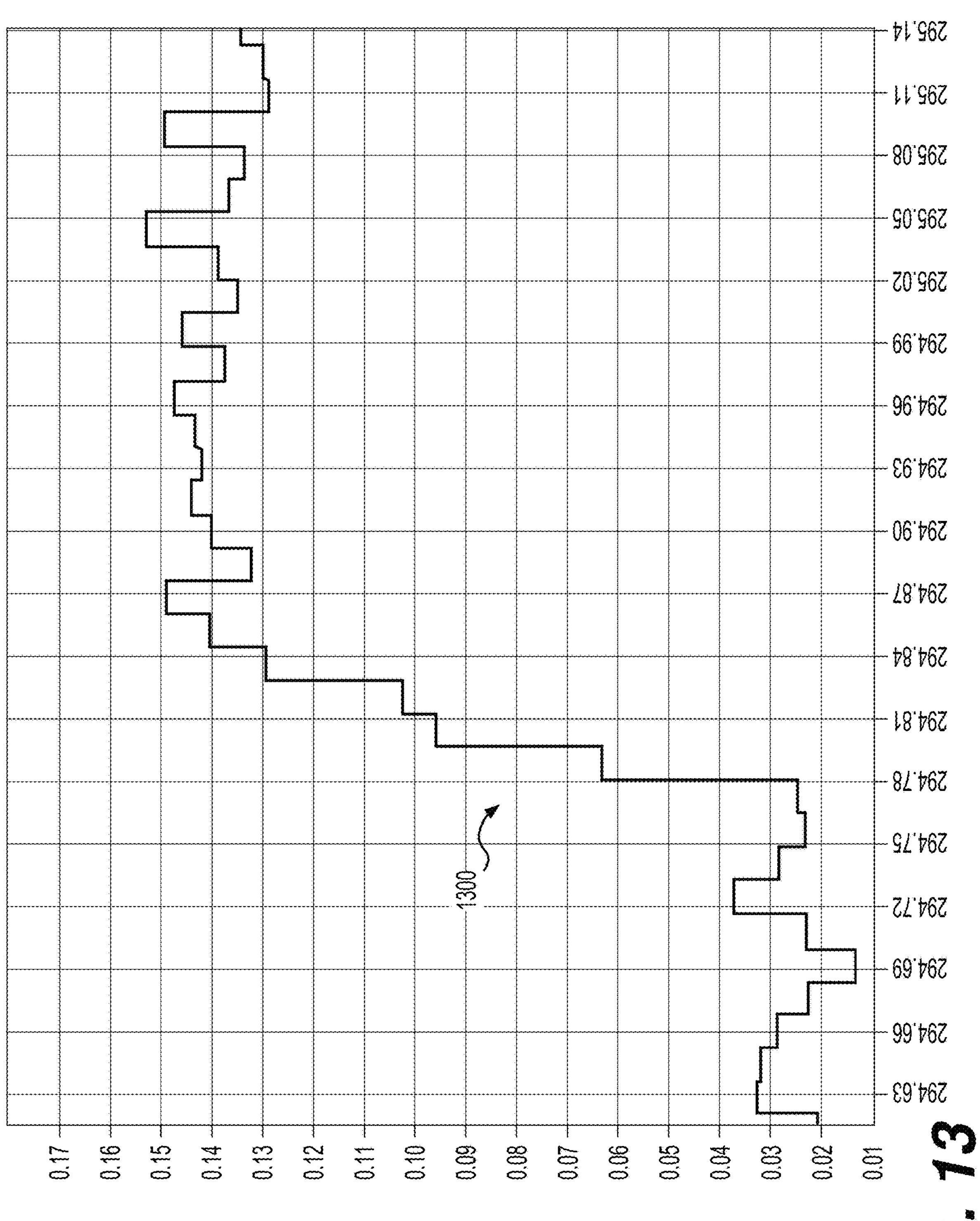
FIG. 13 is a sampled and normalized current profile of a solenoid valve having a failed activation, according to an exemplary embodiment of the present disclosure.

The polynomial model and its parameters may be optimized in block 1116 (e.g., through a recursive or non-recursive estimation process such as least mean square estimation ("LSME") using the current profile. In at least one embodiments, a polynomial fit for the current profile for the valve (e.g., generated in block 1108) may be acquired via a LSME process. In an example embodiment, where the current profile comprises 20 current measurement values (e.g., as shown in FIGS. 12 and 13), a fifth degree polynomial model may be selected. The higher the polynomial degree is, the higher the load may be on the control unit 100, thus resulting in increased processing time and a higher burden to processing power. However, the degree may need to be high enough to capture the behavior of the current profile (e.g., the initial peak 1002, the dip 1004, and subsequent rise 1006), but low enough to be manageable by the control unit 100. The same type of balancing act is also applicable to the number of samples taken. There should be enough samples to capture the current profile behavior correctly, but not too many samples, which may overload the processor (e.g., processor 102). Further, a higher degree polynomial may have undesired behaviors in the fitting process described herein. Thus a degree of the polynomial model may be selected that can capture the "dip" of the current profile well (in the event that valve has successfully activated). However, in the event that there is no dip present in the current profile of the valve (e.g., there is a failed opening of the valve) higher order terms may be estimated to be close to 0.

At block 1116, the polynomial model may be optimized for the current profile through an estimation process (e.g., LMSE). In some embodiments, the polynomial model used in LMSE may be represented as:

$$\gamma_N = \Phi_N \theta + e$$

where $\gamma_N$ is the observation vector (i.e., the samples of current measurements received at block 1104), $\Phi_N$ is the regression matrix, θ is the parameter vector describing the system (e.g., the polynomial model that calculates current from time stamps), and e represents the error of the polynomial fit against the sampled data. Since the sample interval is known and the number of samples are selected (e.g., a sampling interval of every 0.001 s and 120 samples), the regression matrix $\Phi_N$ can be calculated as follows:

$$\Phi_N = [\phi_1 \ \dots \ \phi_N]$$

$$\phi_1^T = [t_1^5, t_1^4, t_1^3, t_1^2, t_1^1, t_1^0]$$

$$\phi_N^T = [t_N^5, t_N^4, t_N^3, t_N^2, t_N^1, t_N^0]$$

In one embodiment, the parameter vector θ can expressed using the following equation:

$$\hat{\theta} = (\Phi_N^T \Phi_N)^{-1} \Phi_N^T \gamma_N,$$

where $\hat{\theta}$ is the solution, based on a minimization of error, in the original equation discussed above, i.e., $\gamma_N = \Phi_N \theta + e$ (all the current samples ($\gamma_N$)). Further, $\hat{\theta}$ may comprise a vector with the coefficients to be used to calculate the current at a given time after activation. Thus, the polynomial model may be optimized by relying on coefficients and/or parameters determined through $\hat{\theta}$. In some embodiments, the estimation process to optimize the polynomial model may be rendered more efficient (e.g., and minimizing the burden on the processor of control unit 100) and/or reliable (e.g., against risks of precision loss) by scaling the time used in the regression matrix, $\Phi_N$ (e.g., by having times be at every 0.1 s, instead of 0.001 s.).

Figure 14:
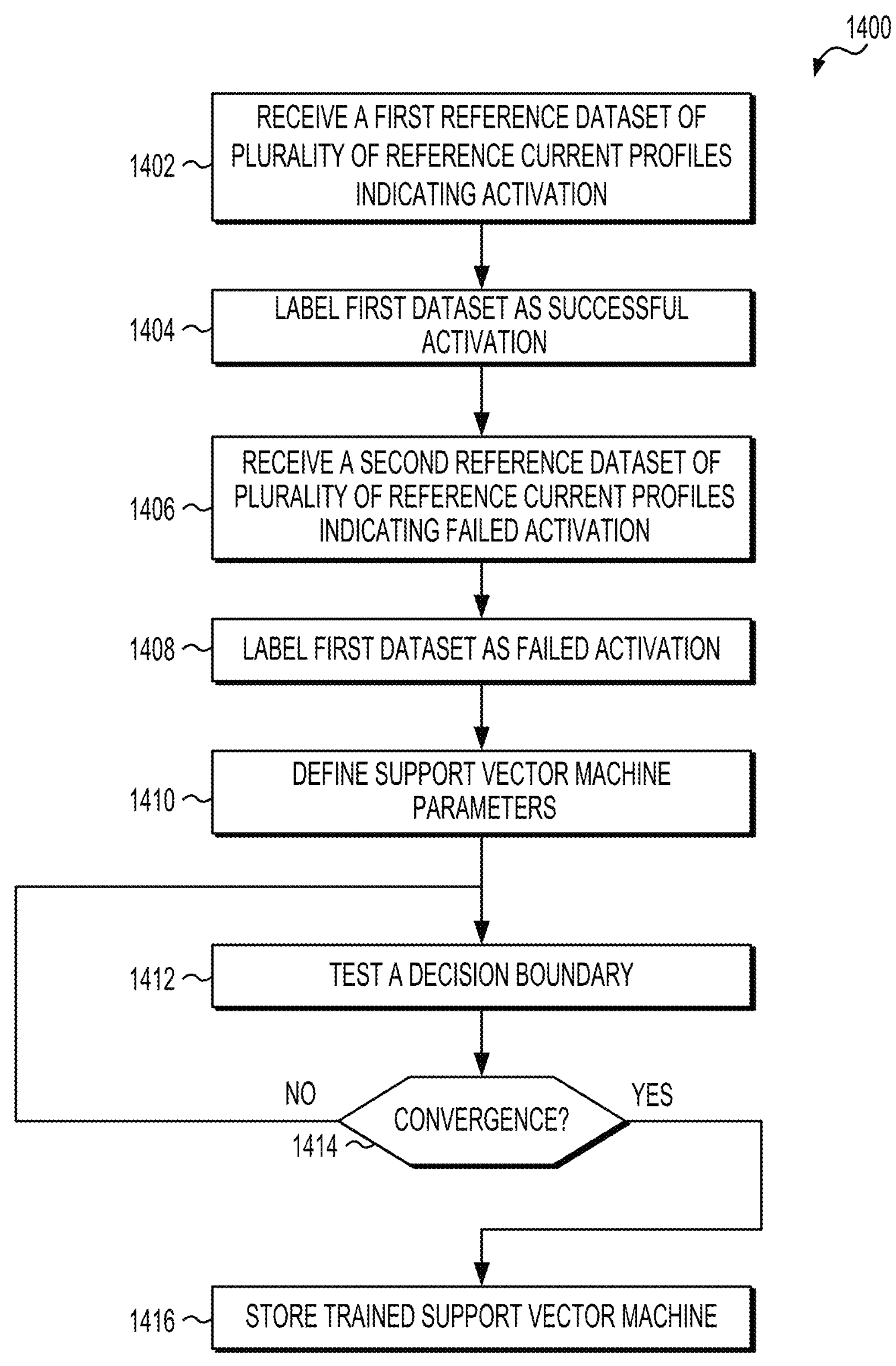
FIG. 14 is a flowchart of an example process for training a classification model for assessing the functionality of a solenoid valve activation, according to an exemplary embodiment of the present disclosure.

At block 1118, the control unit 100 may apply the optimized polynomial model to a trained classification model to determine an activation status for the valve. The classification model may be trained based on reference datasets of current profiles, and/or polynomial models representing such current profiles, labeled with an activation status (e.g., a successful activation or a failed activation). Process 1400 described in FIG. 14 provides an example of at least one embodiment for training such a classification model. The trained classification model, as will be discussed in FIG. 14, may comprise a support vector machine ("SVM"). Also or alternatively, other supervised machine learning models for classifying or distinguishing divergent datasets may be utilized.

The output of applying the optimized polynomial model into the trained classification model may comprise an activation status of a successful activation (e.g., the polynomial model fits the class of polynomial models based on current profiles of valves that had a successful opening) or a failed activation (e.g., the polynomial model fits the class of polynomial models for current profiles of valves that had a failed opening). In some embodiments, there may be additional options for outputs (e.g., no opening, near successful opening, etc.) depending on the labeled training data used to train the classification model. The activation status may thus be determined, and the control unit 100 may identify, at block 1120, whether the valve being assessed had a successful activation (e.g., block 1120—Yes).

If the valve is determined to have had a successful activation (e.g., based on blocks 1106 through 1120), the control unit 100 may determine whether there are additional valves to be assessed (block 1124). If there are additional valves, blocks 1106 through 1120 may be repeated for those additional valves to assess, from their current profiles, whether a successful activation has occurred. If valve 154, 194 is determined to have not had an activation, based on the assessment of its current profile (e.g., block 1120—No), the control unit 100 may alert an operator that the valve is malfunctioned. For example, PD system 10 may generate (e.g., via an indicator display) a warning, caution, and/or danger symbol, or generate and audio or visual cue. After each valve 154, 194 is assessed, and/or after any malfunction has been reported, the control unit 100 may end its assessment of valves for their activation functionality (block 1126).

In some embodiments, alternatives to a polynomial model may be used to represent and/or fit the current profile. For example, a logistic model may be used, such as one represented as: $y(t)=I_{max}(1-e^{-t/\tau})$, where t is the time, $i_{max}$ is the maximum current, y(t) is the current at time t, and $\tau$ is a time constant of the system. The model may be used, for example to effectively fit current profiles corresponding to valves 154, 194 with failed valve openings (i.e., failed activations), and therefore detect valves 154, 194 with failed activations.

In some embodiments, variations of one or more steps of process 1100 may be used to assess the functionality of a solenoid valve deactivation, e.g., closing. For example, after deactivating valves (block 1102), current measurements may be received at a predetermined sampling rate over a predetermined duration (block 1104). For one or more valves to be assessed, a profile of current measurements may be generated using the above described processes (blocks 1104 through 1112). A polynomial model may be applied and optimized to the current profile (blocks 1114 and 1116). The optimized polynomial model estimating the current profile of a given solenoid valve, as it is ordered to deactivate, may then be applied to a trained classification model (e.g., a support vector machine), which can detect whether there is an actual or failed deactivation, e.g., closing, of the solenoid valve (block 1118). The trained classification model for detecting deactivation may be different from the trained classification model for detecting activation, as the former may rely on reference training data of two sets of current profiles associated with (i) successful and (ii) failed valve deactivation, respectively.

FIG. 12 is a sampled and normalized current profile 100 of a solenoid valve 154, 194 having a successful activation, according to an exemplary embodiment of the present disclosure. For example, the current profile 1200 may be generated by the control unit 100 at block 1112 of process 1100 (e.g., after normalizing each current measurement value based on a maximum current). The step-like nature of current profile 1200 (e.g., in contrast to the current profiles shown in FIGS. 10A and 10B) may result from a lower sampling frequency, which may aid in more efficient processing to assess the functionality of valve activation. The increased efficiency as a result of lower sampling rates may allow for quicker and more effective alerts for malfunctioning valves in a PD system 10, thus improving patient care. As previously discussed in relation to FIGS. 10A and 10B, the current profile 1200 may correspond to valve 154, 194 having a successful activation due to a signature "dip" in the current (e.g., at approximately 22 milliseconds). However, in current profiles with lesser sampling rates (e.g., current profile 1200), the "dip" may be difficult to identify. Thus, PD system 10 (via its control unit 100) may rely on process 1100 to determine that current profile 1200 corresponds to a valve having a successful activation.

In contrast, FIG. 13 is a sampled and normalized current profile 1300 of solenoid valve 154, 194 having a failed activation, according to an exemplary embodiment of the present disclosure. Like current profile 1200 in FIG. 12, current profile 1300 may be generated by the control unit 100 at block 1112 of process 1100 (e.g., after normalizing each current measurement value based on a maximum current). The step-like nature of current profile 1300 (e.g., in contrast to the current profiles shown in FIGS. 10A and 10B) may result from a lower sampling frequency, which makes it harder to discern any signature "dip," or lack thereof, to assess whether the current profile 1300 indicates a successful or failed valve opening. However, as previously discussed, process 1100 may be used to determine that current profile 1300 corresponds to a valve having a failed activation.

FIG. 14 is a flowchart of an example process 1400 for training a classification model (e.g., an SVM) for assessing the functionality of a solenoid valve activation, according to an exemplary embodiment of the present disclosure. As previously discussed, process 1400 shows an example embodiment for training a classification model used in block 1118 of process 1100 (e.g., to feed the optimized polynomial model). Process 1400 may be performed by a computing system (e.g., control 100 of PD system 10) having one or more processors (e.g., processor 102). For example, the processor 102 may perform process 1400 based on computer-executable instructions stored in the memory 104. Although, in some embodiments, process 1400 can occur in remote computing systems (e.g., a remote server or big data analytics lab) different from the control unit 100 of PD system 10, process 1400 will be described as being performed by control unit 100 of PD system 10, for ease of explanation.

Process 1400 may begin with the control unit 100 receiving a reference dataset of plurality of current profiles corresponding to valves 154, 194 having a successful activation (block 1402). This reference data set may be referred to as first reference dataset, to distinguish from a reference dataset received at block 1406 (referred to as second reference dataset) of another plurality of current profiles corresponding to valves having a failed activation.

The first reference dataset may be labelled as having an outcome of a successful activation (block 1404). For example, the first reference dataset may be vectorized (e.g., by quantifying its current measurement values) and associated with a binary indicator (e.g., true or "1") indicating the successful activation.

At block 1406, the control unit 100 may receive a second reference dataset of a plurality of reference current profiles corresponding to valves 154, 194 having a failed activation (e.g., the valves failed to open during the duration of time corresponding to the current profile). The second reference dataset may be labelled as having an outcome of a failed activation (block 1408). For example, the second reference dataset may be vectorized (e.g., by quantifying its current measurement values) and associated with a binary indicator (e.g., false or "0") indicating the failed activation.

At block 1410, control unit 100 may define parameters for a classification model (e.g., an SVM) for a supervised training to determine a decision boundary between data corresponding to the successful activation and data corresponding to the failed activation. For example, each dataset, whether it corresponds to the first reference dataset or a second reference dataset, may be based on, or may be fitted to, a polynomial model of a predetermined degree (e.g., fifth degree) (e.g., using LSME methods explained in block 1116 of process 1100). For an n degree polynomial model, the coefficients for each degree up to that n degree may be used as a parameter for a classification model (e.g., an SVM) to plot and/or situate an individual data point (i.e., an observation).

At blocks 1412 and 1414, different decision boundaries may be tested (block 1412) to see how effectively they separate data belonging to first reference dataset from the second reference dataset, until a convergence is reached (block 1414). In some embodiments, a convergence may indicate that the tested decision boundary yields the largest margin between a data point belonging to the first reference dataset and a data point belonging to the second reference dataset. Further, the decision boundary may indicate, which side (e.g., the side of the first reference dataset corresponding to successful activation or the side of the second reference dataset corresponding to failed activation) a given polynomial model may fall into, based on the coefficients for each parameter of the polynomial model.

The trained classification model, for example, a trained support vector machine with parameters for the decision boundary, may be stored (e.g., in memory 104 of control unit 100) at block 1416. The trained support vector machine can thus be used for applying the optimized polynomial model from process 1100 to determine whether the current profile belongs to the side of a successful activation (e.g., the same side as the first reference dataset) or the side of the failed activation (e.g., the same side as the second reference dataset).

A trained classification model, such as a support vector machine, may comprise a supervised learning model that analyzes training data (e.g., a plurality of current profiles used as a reference (referred to herein as reference current profiles), and knowledge of whether each reference current profile corresponds to a successful activation or a failed activation) to automatically learn (e.g., via an iterative error minimization process) relationships between an input data (e.g., various parameters of any given current profile) and two or more discrete outcomes (e.g., whether the current profile corresponds to a successful activation or a failed activation). The learned relationship can then be applied to testing data with an unknown outcome (e.g., a current profile for a valve for which the valve activation state is not known) to determine the outcome (e.g., whether the valve has actually undergone a successful activation). An SVM may be an example of a classification model in which the learned relationship is a decision boundary (e.g., to separate current profiles of valves with successful valve activations from current profiles of valves with failed valve activations).

In some embodiments, variations of one or more steps of process 1400 may be used for training a classification model for assessing the functionality of a solenoid valve deactivation (e.g. whether a valve has actually closed). For example, the first reference dataset may comprise a plurality of reference current profiles indicating a successful deactivation or valve closing (block 1402), while the second reference dataset may comprise a plurality of reference current profiles indicating a failed deactivation or valve closing (block 1406). The first and second reference datasets may be labeled as a successful deactivation (block 1404) and a failed deactivation (block 1408), respectively. The labeled datasets may be used in the training process (blocks 1410 through 1414) and the resulting trained support vector machine may be stored for use (block 1416) in identifying whether a given valve has successfully deactivated.

It should be understood that various changes and modifications to the presently preferred embodiments described herein will be apparent to those skilled in the art. It is therefore intended that such changes and modifications be covered by the appended claims. For example, while the MOSFET and NPN transistors are described as transistors used to assist in noise reduction during solenoid valve activation and deactivation, other transistors may similarly be used to slow down the plunger in the solenoid valves to similarly reduce noise. As another example, while the support vector machine is used to classify current profiles of valves with successful activations from current profiles of valves with failed activations, other machine learning models can be utilized for this classification. As a further example and as discussed herein, the systems and methods of the present disclosure may be used to assess both valve actuation (e.g., whether a valve has actually opened) and valve deactivation (e.g., whether a valve has actually closed). For example, an optimized polynomial model of a current profile of a solenoid valve, as it is ordered to deactivate, may be applied to a trained classification model to determine whether the solenoid valve has actually closed. In yet a further example, any of the solenoid valves discussed herein may, but is not required to be, a solenoid pinch valve. In still a further example, while different valve embodiments have been discussed primarily in connection with peritoneal dialysis ("PD"), the valve embodiments may be used with other medical fluid systems and associated machines, such as ones for hemodialysis ("HD"), hemofiltration ("HF"), hemodiafiltration ("HDF"), and continuous renal replacement treatment ("CRRT").

The invention is claimed as follows:

1. A medical fluid system comprising:

a control unit;

a plurality of metal oxide semiconductor field effect transistors ("MOSFETs") configured to control a plurality of valves, in response to control signals received from the control unit; and a plurality of valves, wherein each valve comprises a housing, a coil, and a plunger, and wherein each valve is configured to allow a flow of medical fluid through a tube by applying, via an associated MOSFET of the plurality of MOSFETs, a voltage to the corresponding coil to move the corresponding plunger within the corresponding housing, the control unit comprising at least one processor and at least one memory, wherein the at least one memory stores instructions that, when executed by the at least one processor, cause the at least one processor to:

transmit, to one of the MOSFETs, a high digital control signal, wherein the MOSFET, responsive to the high digital control signal, causes a corresponding valve to ramp up the voltage applied to a corresponding coil until the voltage reaches a predetermined input voltage, Vin, and wherein the ramping up of the voltage applied to the corresponding coil causes the corresponding plunger to move in a manner in which sound generated by the corresponding plunger is reduced in comparison to operation without the MOSFET.

2. The medical fluid system of claim 1, wherein each valve is configured to close the flow of medical fluid through the tube by un-applying, via the corresponding MOSFET, the voltage to the corresponding coil so that the corresponding plunger moves in an opposite direction to occlude the corresponding tube.

3. The medical fluid system of claim 2, wherein the instructions, when executed by the at least one processor, further cause the at least one processor to:

transmit, to the MOSFET of the plurality of MOSFETs, a low digital control signal, wherein the MOSFET, responsive to the low digital control signal, causes the corresponding valve to ramp down the voltage applied to the corresponding coil until the voltage reaches 0 volts, and wherein the ramping down of the voltage applied to the corresponding coil causes the corresponding plunger to move in an opposite direction and in a manner in which sound generated by the corresponding plunger is reduced in comparison to operation without the MOSFET.

4. The medical fluid system of claim 3, further comprising:

at least one resistor serially arranged between the control unit and the MOSFET, wherein a duration of the ramping up of the voltage applied to the corresponding coil is based on at least one resistance value of the corresponding at least one resistor, and wherein a duration of the ramping down of the voltage applied to the corresponding coil is based on the at least one resistance value of the corresponding at least one resistor.

5. The medical fluid system of claim 4, further comprising:

at least one capacitor serially arranged between the control unit and the MOSFET, wherein the duration of the ramping up of the voltage applied to the corresponding coil is further based on capacitance values of the corresponding at least one capacitor, and wherein the duration of the ramping down of the voltage applied to the corresponding coil is further based on the capacitance values of the corresponding at least one capacitor.

6. The medical fluid system of claim 1, further comprising an initial ramp offset circuit comprising a feedback resistor.

7. The medical fluid system of claim 6, wherein the instructions, when executed, further cause the processor to:

apply, via the initial ramp offset circuit, an offset voltage set below the voltage applied to the corresponding coil when ramping up the input current to the MOSFET.

8. A medical fluid system comprising:

a control unit;

a plurality of input/output ("I/O") nodes configured to control a plurality of valves via pulse width modulation ("PWM") signals, in response to control signals received from the control unit; and a plurality of valves, wherein each valve comprises a housing, a coil, and a plunger, and wherein each valve is configured to allow a flow of medical fluid through a tube by applying, via an associated I/O node of the plurality of I/O nodes, a voltage to the corresponding coil to move the corresponding plunger within the corresponding housing, the control unit comprising at least one processor and at least one memory, wherein the at least one memory stores instructions that, when executed by the at least one processor, cause the at least one processor to:

transmit, to an I/O node of the plurality of I/O nodes, a control signal causing the I/O node to apply and ramp up a PWM signal to the corresponding coil, and wherein the ramping up of the PWM signal causes the corresponding plunger to move in a manner in which sound generated by the corresponding plunger is reduced in comparison to operation without the PWM signal.

9. The medical fluid system of claim 8, wherein ramping up of the PWM signal comprises ramping up a duty cycle of a pulsed application of the voltage to the corresponding coil from 0% to 100% during 50 ms.

10. The medical fluid system of claim 8, wherein the instructions, when executed, further cause the processor to:

after the plunger reaches an end position, transmit, to the I/O node, a second control signal causing the I/O node to ramp down the PWM signal to the corresponding coil to a duty cycle that is at least 25%.

11. The medical fluid system of claim 10, wherein the second control signal causes the I/O node to ramp down the PWM signal to the corresponding coil to a duty cycle that is at least 50%.

12. The medical fluid system of claim 10, wherein each valve is configured to close the flow of medical fluid through the tube by un-applying, via the corresponding I/O node, the voltage to the corresponding coil so that the corresponding plunger moves in an opposite direction to occlude the corresponding tube.

13. The medical fluid system of claim 12, wherein the instructions, when executed by the at least one processor, further cause the at least one processor to:

transmit, to the I/O node, a third control signal causing the I/O node to ramp down the PWM signal to the corresponding coil to a duty cycle of 0%, wherein the ramping down of the PWM signal to the corresponding coil causes the corresponding plunger to move in an opposite direction and in manner in which sound generated by the corresponding plunger is reduced in comparison to operation without the PWM signal.

14. The medical fluid system of claim 13, wherein the ramping down of the PWM signal to the corresponding coil to the duty cycle of 0% occurs during a time between 25 to 75 ms.

15. The medical fluid system of claim 13, further comprising:

at least one resistor serially arranged between the control unit and the I/O node, wherein a duration of the ramping up of the PWM signal is based on resistance values of the corresponding at least one resistor, and wherein a duration of the ramping down of the PWM signal is based on the resistance values of the corresponding at least one resistor.

16. The medical fluid system of claim 13, further comprising:

at least one capacitor serially arranged between the control unit and the I/O node, wherein the duration of the ramping up of the PWM signal is further based on capacitance values of the corresponding at least one capacitor, and wherein the duration of the ramping down of the PWM signal is further based on the capacitance values of the corresponding at least one capacitor.

* * * * *